US009452265B2

(12) United States Patent
Quinn et al.

(10) Patent No.: US 9,452,265 B2
(45) Date of Patent: Sep. 27, 2016

(54) END OF INJECTION INDICATOR FOR INJECTION PEN

(75) Inventors: Michael V Quinn, East Hanover, NJ (US); Richard Cronenberg, Mahway, NJ (US); Gautam Shetty, Ridgewood, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 14/005,603

(22) PCT Filed: Mar. 16, 2012
(Under 37 CFR 1.47)

(86) PCT No.: PCT/US2012/029545
§ 371 (c)(1),
(2), (4) Date: Nov. 26, 2013

(87) PCT Pub. No.: WO2012/129120
PCT Pub. Date: Sep. 27, 2012

(65) Prior Publication Data
US 2014/0163477 A1    Jun. 12, 2014

Related U.S. Application Data

(60) Provisional application No. 61/457,403, filed on Mar. 18, 2011.

(51) Int. Cl.
*A61M 5/315* (2006.01)
(52) U.S. Cl.
CPC ....... *A61M 5/3157* (2013.01); *A61M 5/31551* (2013.01); *A61M 5/31585* (2013.01); *A61M 2205/581* (2013.01); *A61M 2205/583* (2013.01)

(58) Field of Classification Search
CPC ................ A61M 2205/581; A61M 2205/583; A61M 5/31551; A61M 5/3157; A61M 5/31585
USPC .................................. 604/71, 207, 211, 246
See application file for complete search history.

(56) References Cited

U.S. PATENT DOCUMENTS 5,626,566 A    5/1997    Petersen
6,666,849 B1 *    12/2003    Marshall ........... A61M 5/31553
604/131

(Continued)

FOREIGN PATENT DOCUMENTS

GB    2 443 390 A    5/2008
JP    2009-517157 A    4/2009

(Continued)

OTHER PUBLICATIONS

European Search Report, Issued in Application No. EP 12 76 0555, Dated Jul. 21, 2014, 7 pages.

*Primary Examiner* — Jason Flick
(74) *Attorney, Agent, or Firm* — Dickinson Wright PLLC

(57) ABSTRACT

A medication injection pen (50) includes a housing (1) and a dose set knob (2) rotatably connected to the housing (1) for setting a dose. An indicator member (200) is movable between an visible position indicating a zero position of the dose set knob (2) and a non-visible position indicating a non-zero position of the dose set knob (2). The indicator member is visible to a user in the visible position and not visible in the non-visible position. The dose set knob is in the zero position when a set dose has been completely administered. Accordingly, a visible indication is provided to a user when a set dose has been completely administered.

20 Claims, 20 Drawing Sheets

(56) References Cited

U.S. PATENT DOCUMENTS

| | | | |
|---|---|---|---|
| 6,899,699 B2* | 5/2005 | Enggaard | 604/246 |
| 2005/0261634 A1* | 11/2005 | Karlsson | 604/197 |
| 2006/0229570 A1 | 10/2006 | Lovell et al. | |
| 2009/0012479 A1 | 1/2009 | Moller | |
| 2009/0247951 A1 | 10/2009 | Kohlbrenner | |
| 2010/0069845 A1* | 3/2010 | Marshall et al. | 604/135 |
| 2010/0152667 A1 | 6/2010 | Kietzmann | |

FOREIGN PATENT DOCUMENTS

| | | |
|---|---|---|
| JP | 2010-503430 A | 2/2010 |
| JP | 2010-508114 A | 3/2010 |
| JP | 2011-506016 A | 3/2011 |
| WO | 2009/080775 A1 | 7/2009 |
| WO | 2010/115670 A1 | 10/2010 |

\* cited by examiner

END OF INJECTION INDICATOR FOR INJECTION PEN

This application claims the benefit under 35 U.S.C. §119 (e) of U.S. Provisional Patent Application Ser. No. 61/457,403, filed on Mar. 18, 2011, which is hereby incorporated by reference in its entirety.

FIELD OF THE INVENTION

The invention relates to a multiple use pen-type injection device with an end of injection indicator to signal to a user that a set dose was completely injected.

BACKGROUND OF THE INVENTION

Various medication injection pen devices are known in the prior art. Many injection pen devices require a user to set a desired dose whereupon a dose dial, a driver, or some other element moves a distance out of a main pen body corresponding to the set dose. To inject the dose in such injection pens, the user then pushes a button or some other feature which generally returns the dose dial or driver to its initial position in the main pen body while injecting the set dose. In many such pens, the user must continue pressing the push button until the set dose is completed. However, one problem with many of these pens is that there is no indication to the user that the set dose was completely administered. Thus, the user may prematurely release the push button thinking the injection process is complete without being informed otherwise. In some situations, this could pose a risk for the user because the prescribed dose was not fully injected. Accordingly, there is a need to provide one or more of a visible, tactile and audible indication to a user when the set dose has been completely administered.

SUMMARY OF THE INVENTION

Exemplary embodiments of the present invention address at least the above problems and/or disadvantages and provide at least the advantages described below.

In accordance with an exemplary embodiment of the present invention, a medication injection pen includes a housing and a dose set knob rotatably connected to the housing for setting a dose. An indicator member is movable between a visible position indicating a zero position of the dose set knob and a non-visible position indicating a non-zero position of the dose set knob. The indicator member is visible to a user in the visible position and not visible in the non-visible position. The dose set knob is in the zero position when a set dose has been completely administered. Accordingly, a visible indication is provided to a user when a set dose has been completely administered.

In accordance with another exemplary embodiment of the present invention, a medication injection pen includes a housing and a dose set knob rotatably connected to the housing for setting a dose. A window is disposed in the housing such that a portion of the outer surface of the dose set knob is visible in the window to indicate a zero position of the dose set knob and the portion of the outer surface of the dose set knob is not visible in the window to indicate the non-zero position. The dose set knob is in the zero position when a set dose has been completely administered.

Additional objects, advantages and salient features of exemplary embodiments of the present invention will become apparent to those skilled in the art from the following detailed description, which, taken in conjunction with the annexed drawings, discloses exemplary embodiments of the present invention.

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings in which.

Throughout the drawings, like reference numerals will be understood to refer to like elements, features and structures.

DETAILED DESCRIPTION OF EXEMPLARY EMBODIMENTS

The matters exemplified in this description are provided to assist in a comprehensive understanding of exemplary embodiments of the invention with reference to the accompanying drawing figures. Accordingly, those of ordinary skill in the art will recognize that various changes and modifications of the exemplary embodiments described herein can be made without departing from the scope and spirit of the disclosed embodiments. Also, descriptions of well-known functions and constructions are omitted for clarity and conciseness.

Figure 1:
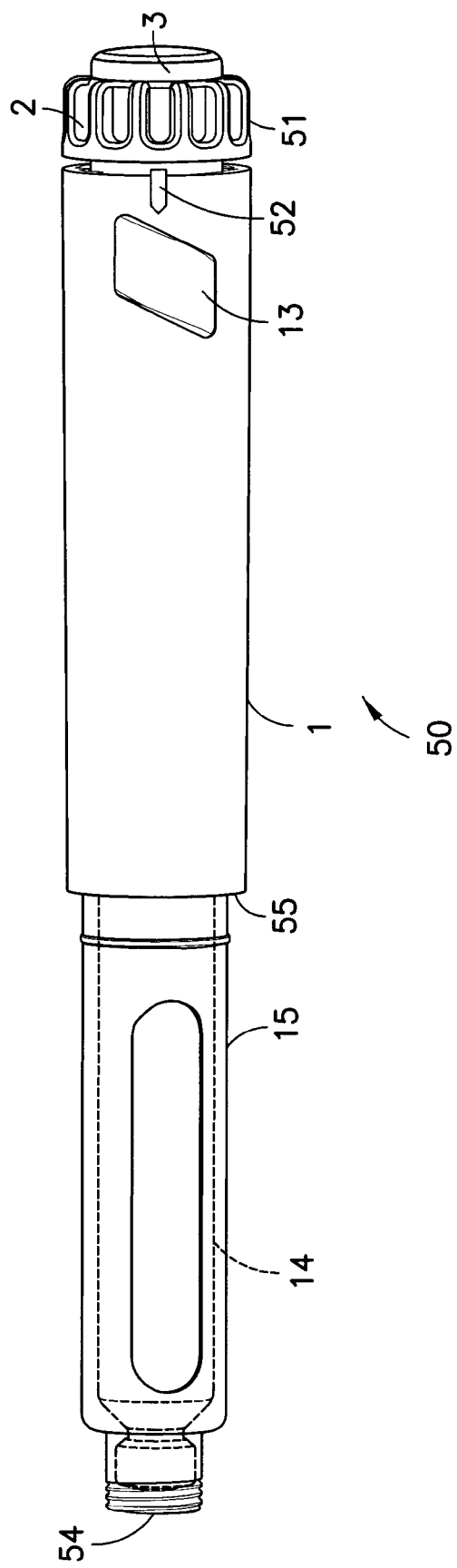
FIG. 1 is an elevational view of an injection pen according to an exemplary embodiment of the present invention.

FIG. 1 depicts a view of an injection pen 50 according to an exemplary embodiment of the present invention. As shown, the injection pen 50 includes an upper pen body 1, which houses a plurality of dose setting and injection components. The upper body 1 is connected to a cartridge housing 15, which houses a medication cartridge 14. The cartridge housing 15 is preferably transparent or translucent. As shown, the injection pen includes a dose set knob 2 that includes a knob-like portion 51 that is rotated by a user to set a desired dose. The dose set knob 2 also includes a plurality of numerals corresponding to a number of dosage units that is visible through a window 13 provided on the upper body 1. A user rotates the dose set knob 2 until the desired dose is visible in the window 13. The body 1 may include an arrow or other indicator 52 to precisely indicate the set dose.

Once the desired dose is set, a user presses the button 3 until the set dosage amount is completely injected.

Figure 2:
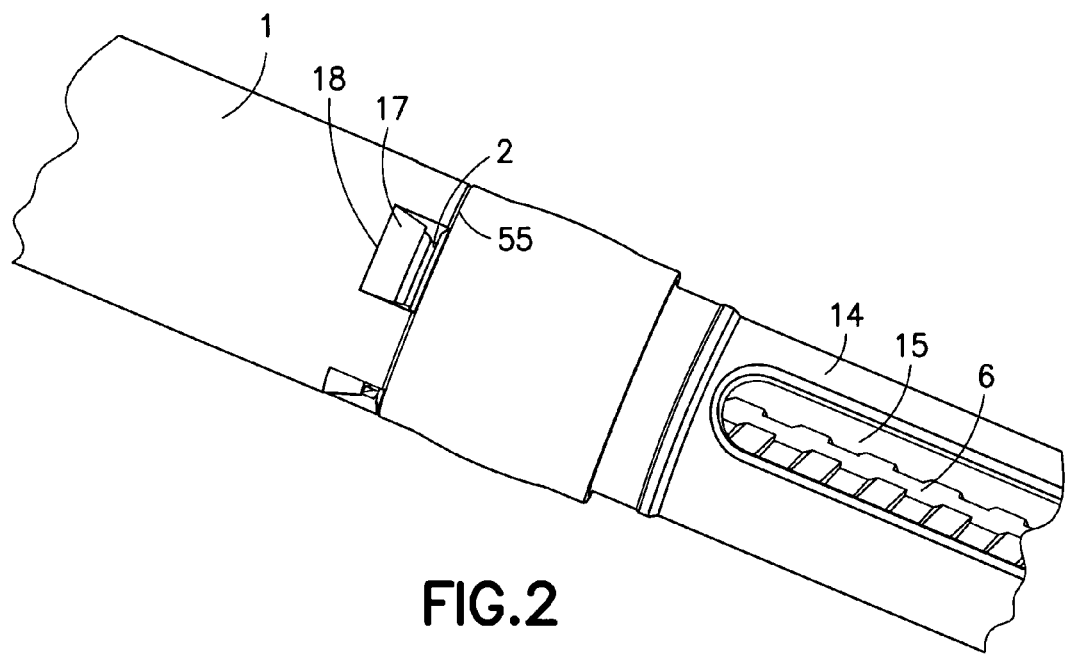
FIG. 2 is a perspective view of an end of injection indicator when the indicator is visible according to a first exemplary embodiment of the present invention.
Figure 6:
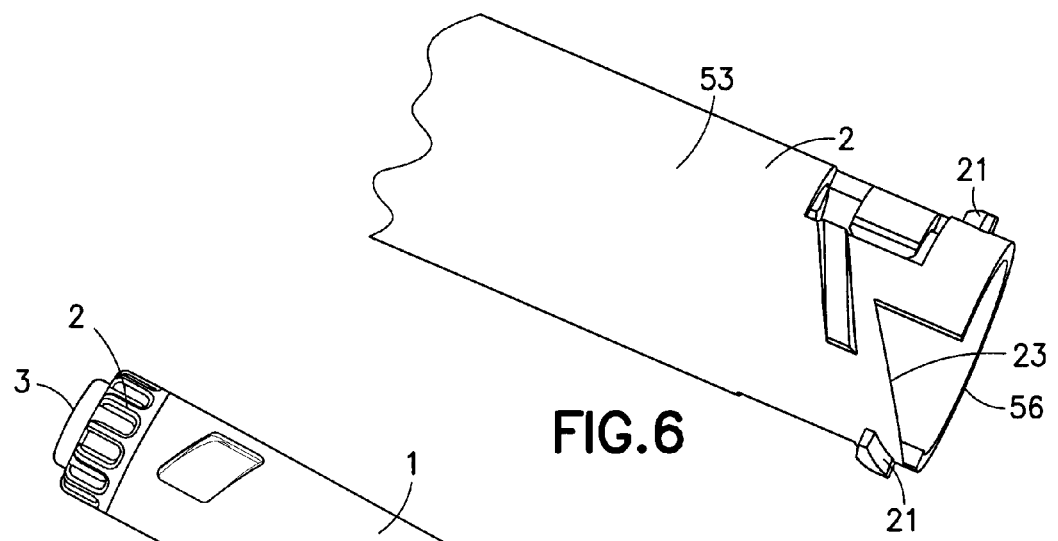
FIG. 6 is a perspective view of a dose set knob in the embodiments of FIGS. 2-5.
Figure 21:
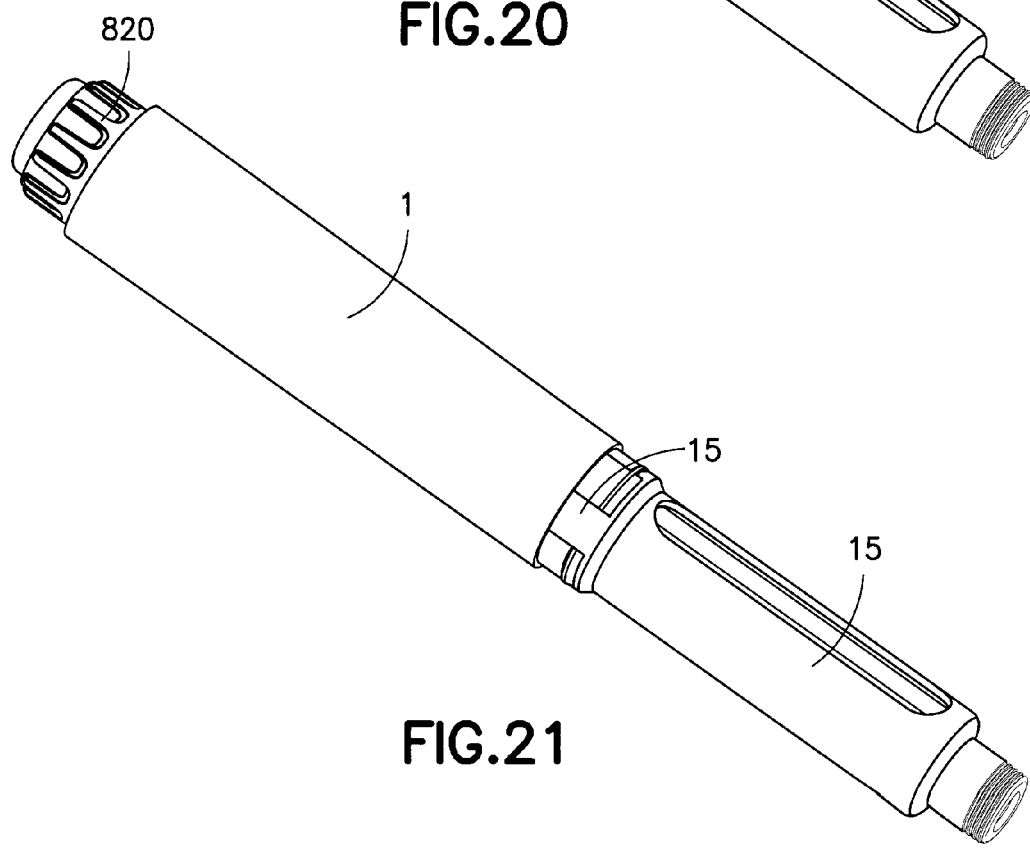
FIG. 21 is a perspective view of the injection pen of FIG. 20 with the indicator member shown in a non-visible position.

To set a dose using the injection pen device 50, the user rotates the knob-like portion 51 of the dose set knob 2 relative to the pen upper body 1. The outer surface 53 of the dose set knob 2 includes a thread 21, as shown in FIG. 6, that is in threaded engagement with a plurality of threads (not shown) provided on an inner surface of the pen body 1. Accordingly, as the dose set knob 2 is rotated relative to the pen body 1, the dose set knob 2 screws or advances a distance out of the pen body 1, as shown in FIG. 21. Once a desired dose is set, the user pushes the push button 3 to initiate injection. As the user continues to press the button 3, the dose set knob 2 is caused to rotate and screw back down into the body via the thread engagement between external thread 21 on the dose set knob 2 and the internal threads in the upper body 1. Rotation of the dose set knob 2 may then be transferred to a driver or other element that causes a piston rod or lead screw 6 to move into cartridge 14 to inject the set dose, as shown in FIG. 2. A more detailed description of the operation of an exemplary injection pen device can be found in U.S. Provisional Patent Application No. 61/457,391, filed on Mar. 16, 2011, and in related International Patent Application No. PCT/US2012/029308, filed on Mar. 15, 2012, both applications entitled "Multiple Use Disposable Injection Pen", and are hereby incorporated by reference in their entirety.

The injection process is completed when the dose set knob 2 returns to its initial or '0' dose position inside pen body 1, such that it is blocked from further rotation and or axial movement in the injection direction, i.e., toward a distal end 54 of the injection pen 50 as shown in FIG. 1. According to the first exemplary embodiment shown in FIG. 2, the pen upper body 1 may include one or more windows 17, through which a portion of the dose set knob 2 is visible only when the dose set knob 2 is at a '0' dose position, such as at the end of injection, when the dose set knob 2 returns to its initial position. The window 17 is disposed in the pen upper body 1 adjacent a distal end 55 of the pen upper body 1. Accordingly, a user can be assured that the injection process is complete only when a portion of the dose set knob is visible through the window 17. Preferably, an elongated side 18 of the window 17 is substantially perpendicular to a longitudinal axis of the pen upper body 1.

Figure 3:
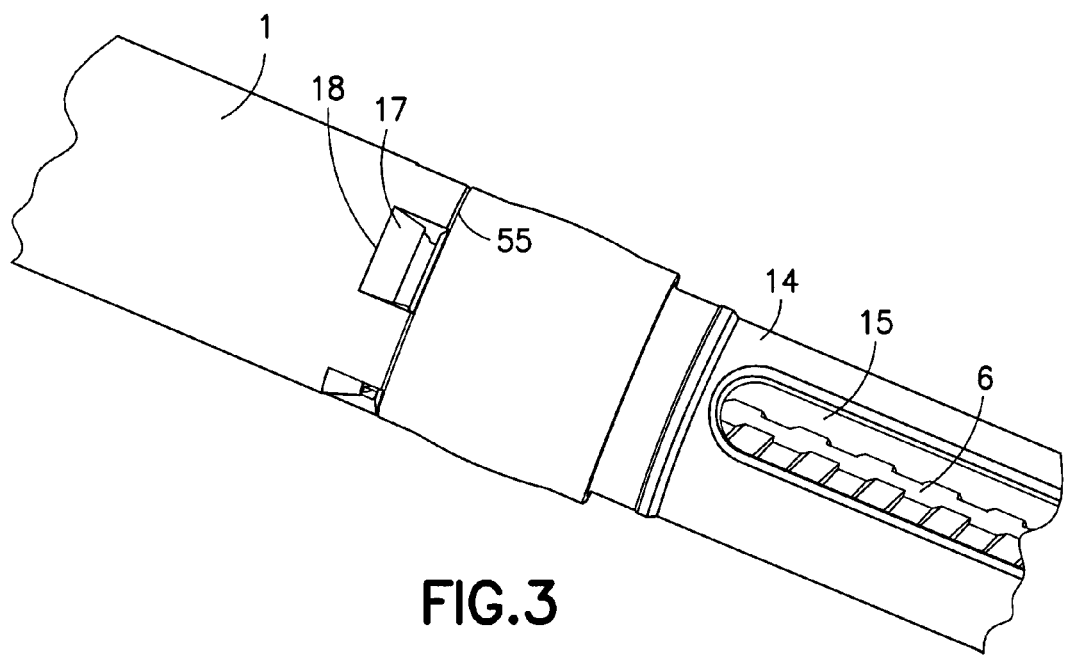
FIG. 3 is a perspective view of the end of injection indicator of FIG. 2 when the indicator is not visible.

When the dose set knob 2 is in the initial position, a distal end 56 (FIG. 6) of the dose set knob 2 is substantially adjacent the distal end 55 of the pen upper body 1 such that a portion of the dose set knob 2 is visible through the window 17 in the pen upper body 1. When a dose is being set, the dose set knob 2 is advance in a distal direction out of the upper pen body, as shown in FIG. 21, such that the distal end 56 of the dose set knob 2 is advanced proximally of the window 17 in the pen upper body 1. Thus, the dose set knob 2 is not visible through the window 17, as shown in FIG. 3. As shown, the dose set knob 2 is not at a '0' dose position, thus either a dose is set, or the injection process is not completed. When the dose is completed, the dose set knob 2 is again visible through the window 17 in the pen upper body 1 because the distal end 56 of the dose set knob 2 is returned to its initial position substantially adjacent the distal end 55 of the pen upper body 1.

Figure 4:
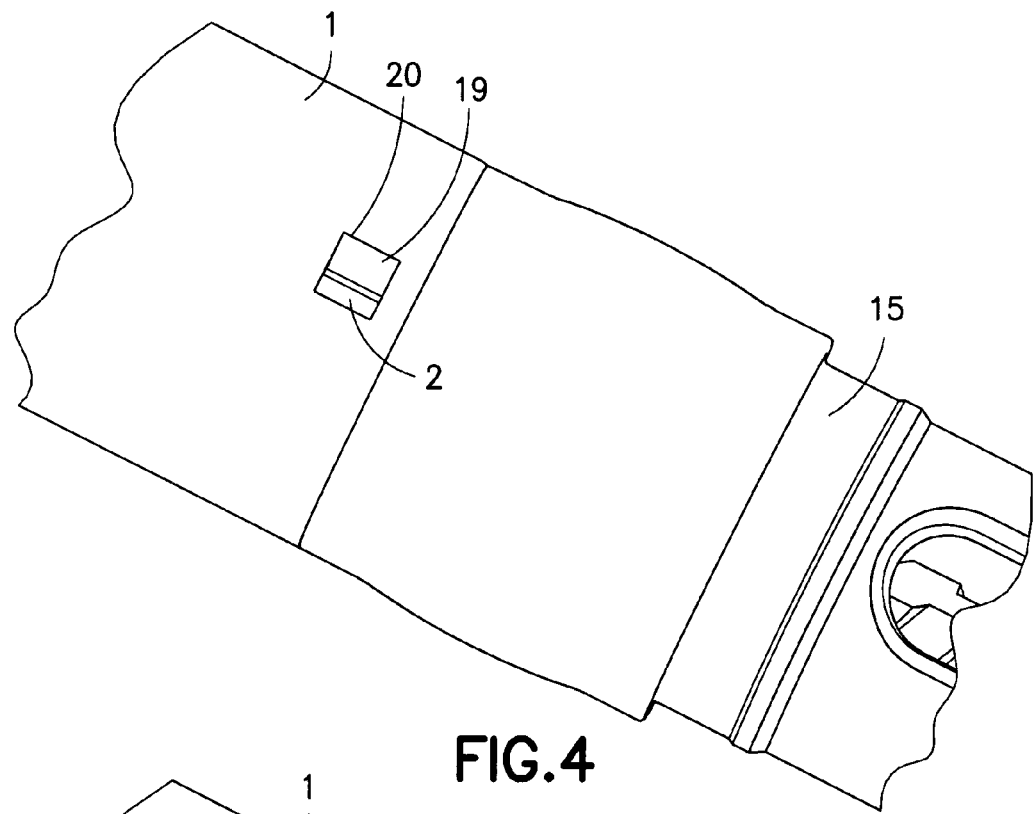
FIG. 4 is a perspective view of an end of injection indicator when the indicator is visible according to a second exemplary embodiment of the present invention.
Figure 5:
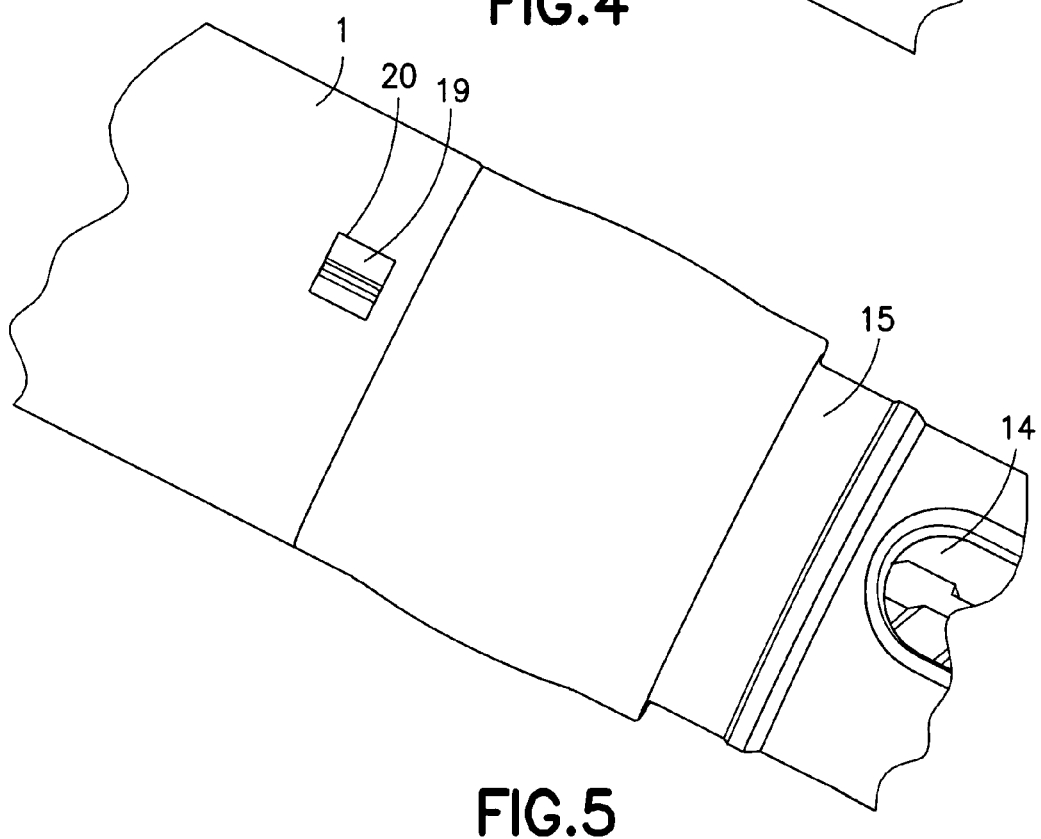
FIG. 5 is a perspective view of the end of injection of FIG. 3 when the indicator is not visible.

An end of injection indicator in accordance with a second exemplary embodiment is shown in FIGS. 4 and 5, which illustrate an injection pen substantially similar to that of FIGS. 2 and 3. A window 19 is disposed in the upper pen body 1, as shown in FIGS. 4 and 5. The window 19 has a different orientation than that of the window 17 of FIGS. 2 and 3. The window 19 has an elongated dimension 20 that is substantially parallel to a longitudinal axis of the pen upper body 1, as opposed to the elongated dimension 18 of the window 17 being substantially perpendicular to the longitudinal axis of the pen upper body 1 as shown in FIGS. 2 and 3.

The end of injection indicator of FIGS. 4 and 5 operates substantially similarly to that of FIGS. 2 and 3. When the dose set knob 2 is not visible through the window 19, as shown in FIG. 5, the dose set knob 2 is not at an initial or '0' dose position, i.e., a dose is being set or has not been completed. When the dose set knob 2 is visible through the window 19, as shown in FIG. 4, the dose set knob 2 is in the initial or '0' dose position.

The dose set knob 2 shown in FIG. 6 can be used with the exemplary embodiments described above with respect to FIGS. 2-5. As shown, the dose set knob 2 is of a generally cylindrical shape. To ensure that no portion of the dose set knob 2 is visible through the window 17 or 19 until the dose set knob 2 is in the initial or '0' dose position, the dose set knob 2 may include a cut-away portion 23. As shown in FIG. 6, the cut-away portion 23 is formed by an inverted substantially V-shaped cut made at the distal end 56 of the dose set knob 2. Because the dose set knob 2 rotates to return to the '0' dose position during an injection, the cut-away portion 23 is preferably removed from a portion of the outer surface as shown. Thus, even when the dose set knob 2 is very close to returning to its initial or '0' dose position, no portion of the dose set knob 2 is visible through the window 17 or 19 until the dose set knob 2 is fully rotated back into the pen upper body 1. Alternatively, instead of providing a cut-away portion 23 of the dose set knob 2, a printed line or block can be provided on a portion of the outer surface 53 of the dose set knob 2 that would only be visible when the dose set knob 2 is in the '0' dose position. Additionally, while the exemplary embodiments shown in FIGS. 2-5 illustrate only a single window near the distal end 55 of the upper pen body 1, a plurality of windows can be utilized in various positions on the pen upper body 1.

Figure 7:
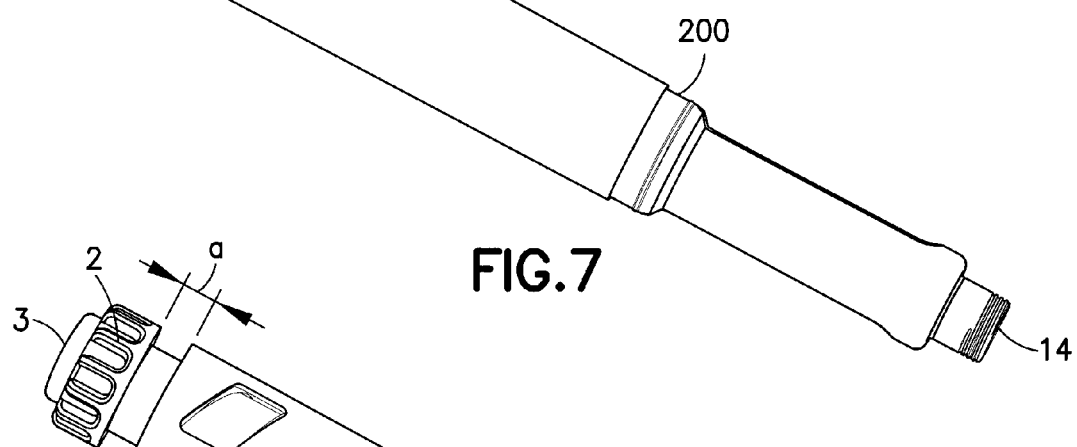
FIG. 7 is a perspective view of an end of injection indicator when an indicator member is visible according to a third exemplary embodiment of the present invention.
Figure 8:
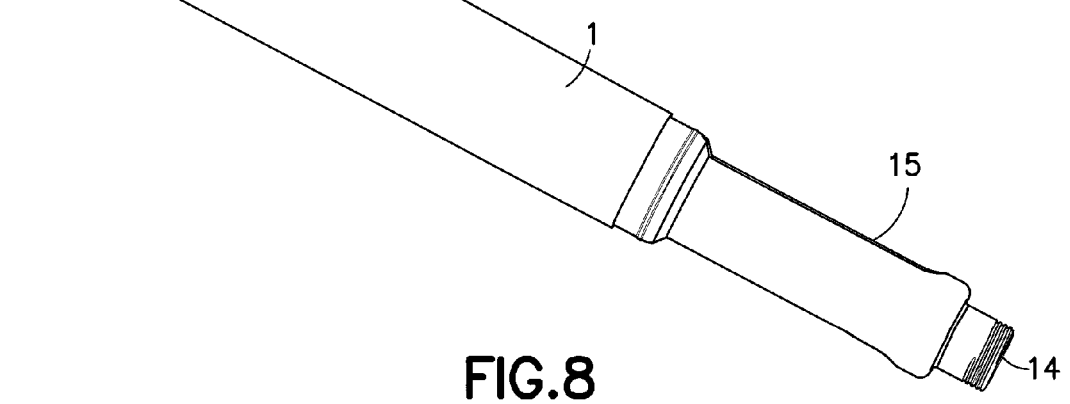
FIG. 8 is a perspective view of the end of injection indicator of FIG. 7 when the indicator member is not visible.

An end of injection indicator according to a third exemplary embodiment of the present invention is shown in FIGS. 7 and 8. An indicator member 200 is in the visible or exposed position and is visible only when the dose set knob 2 is in the '0' dose or initial position as shown in FIG. 7. Accordingly, as shown in FIG. 8, when the dose set knob 2 is not in its initial position, as evident by the gap 'a' between the dose set knob 2 and the pen upper body 1, the indicator member 200 is no longer in the visible position. The exposed indicator member 200 is more readily visible to the user when the dose set knob 2 is in its initial or end of injection position due to the larger size of the indicator member 200. The cartridge housing 15 is preferably transparent or translucent to facilitate visibility of the indicator member 200 in the visible position.

Figure 9:
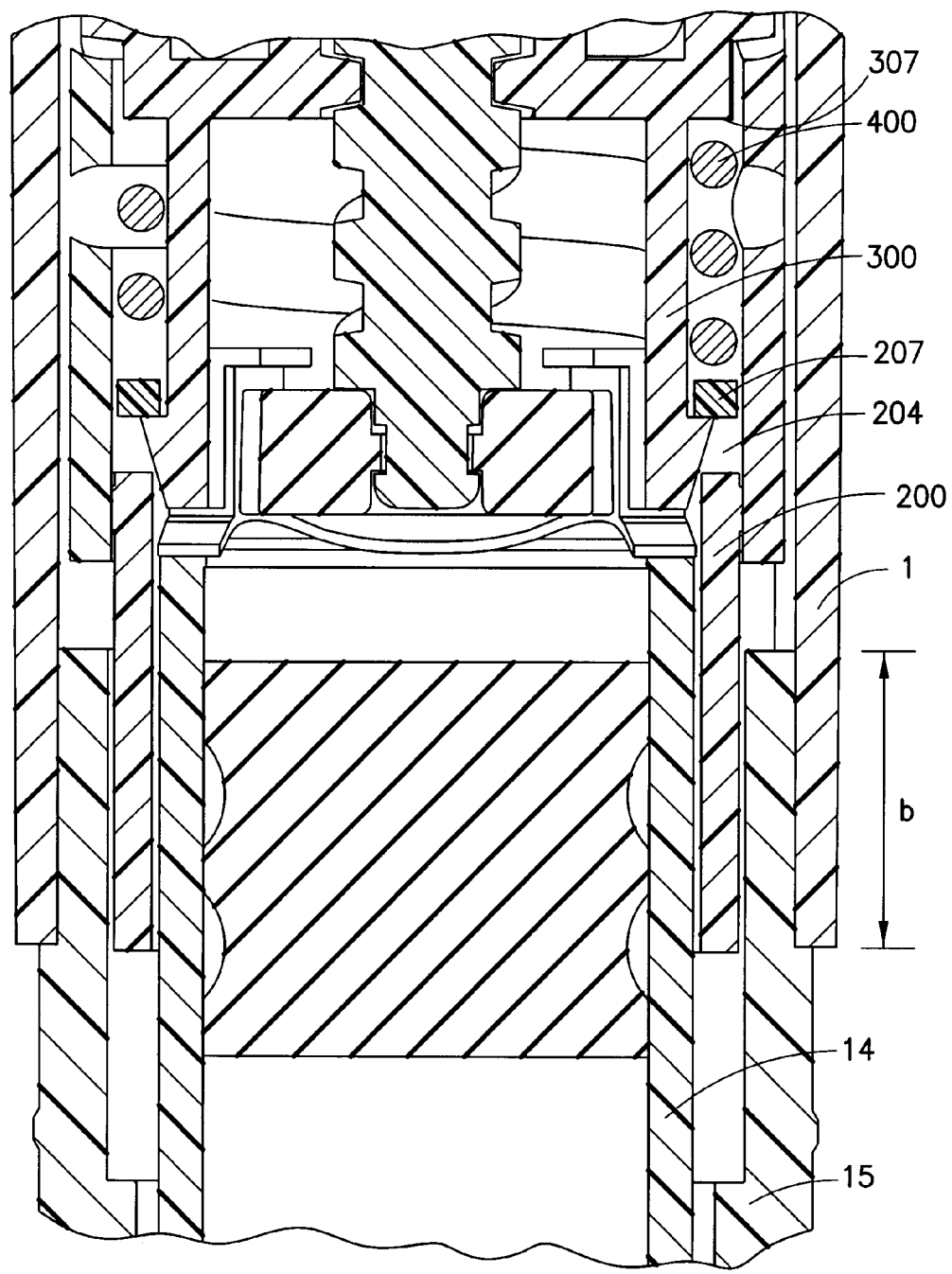
FIG. 9 is an elevational view in cross-section of the end of injection indicator of FIGS. 7 and 8.

The energy used to activate the indicator member 200 of FIGS. 7 and 8 is stored during the dose setting action performed by the user. To facilitate the injection process, the force required to release the indicator member 200 to the visible position is preferably minimal and unnoticeable to the user. A cross-section of an end of injection mechanism to expose the indicator member 200 of FIGS. 7 and 8 is shown in FIG. 9. Operation of the injection mechanism is shown in FIGS. 10-13, in which the pen body 1 and the cartridge holder 15 are removed to more clearly illustrate the operation thereof.

Figure 10:
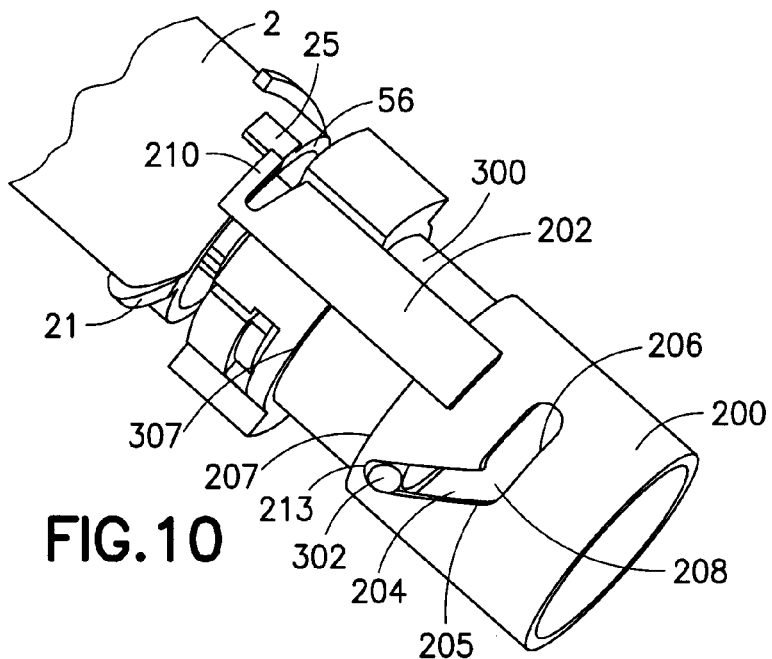
FIG. 10 is a perspective view of the end of injection indicator of FIG. 7 with the indicator member in a visible position.

As shown in FIG. 10, the indicator member 200 is of a substantially cylindrical shape and coaxially surrounds an insert 300. The insert 300 is held axially and rotatably fixed with respect to a pen upper body or housing 1, as shown in FIG. 9. FIGS. 9 and 10 depict the indicator member 200 in the visible or exposed position, visible to a user. As such, the dose set knob 2 is in its initial or '0' dose position. As shown in FIG. 9, a portion of the indicator element 200, represented by a length 'b', is visible between the pen body 1 and the cartridge housing 15 when the indicator member 200 is in the visible position. The cartridge housing 15 is preferably transparent or translucent to facilitate visibility of the indicator member 200. A compression spring element 400 is provided coaxially surrounding the insert 300 between a ledge 307 of the insert member 300 and a ledge 207 of the indicator member 200. In this position, the spring element 400 is biasing the indicator member 200 away from the dose set knob 2 to expose the indicator member 200 to the user. The indicator member 200 is connected to the insert member 300 via engagement between a boss 302 on the insert member 300 and a track 204 of the indicator member 200. The indicator member 200 is rotatable with respect to the insert member 300. The rotatable movement of the indicator member 200 is determined by the configuration of the track 204 in the indicator member 200.

As shown in FIG. 10, the track 204 has a first or inclined portion 205 extending in a distal direction at an angle to the longitudinal axis of the pen upper body 1. A second or horizontal portion 206 of the track 204 extends substantially perpendicular to the longitudinal axis of the pen upper body 1 from an end 208 of the first portion 205 of the track 204.

Figure 11:
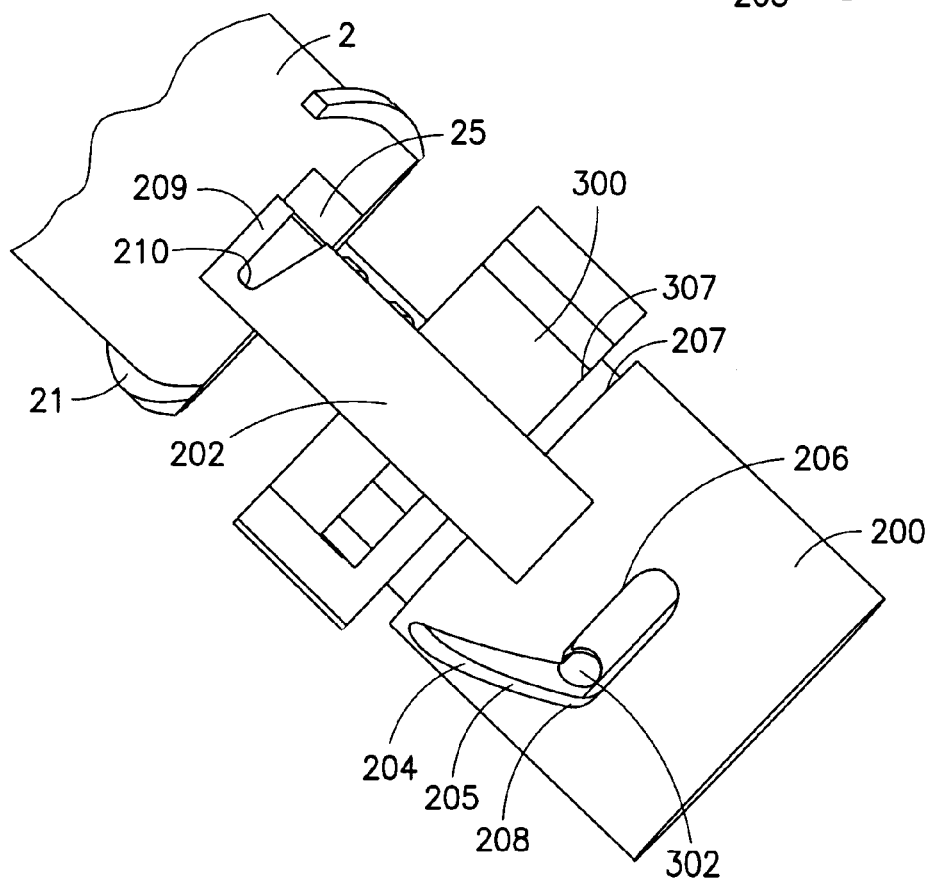
FIG. 11 is a perspective view of the end of injection indicator of FIG. 7 in which a lug of a dose set knob engages the indicator member to retract the indicator member.
Figure 12:
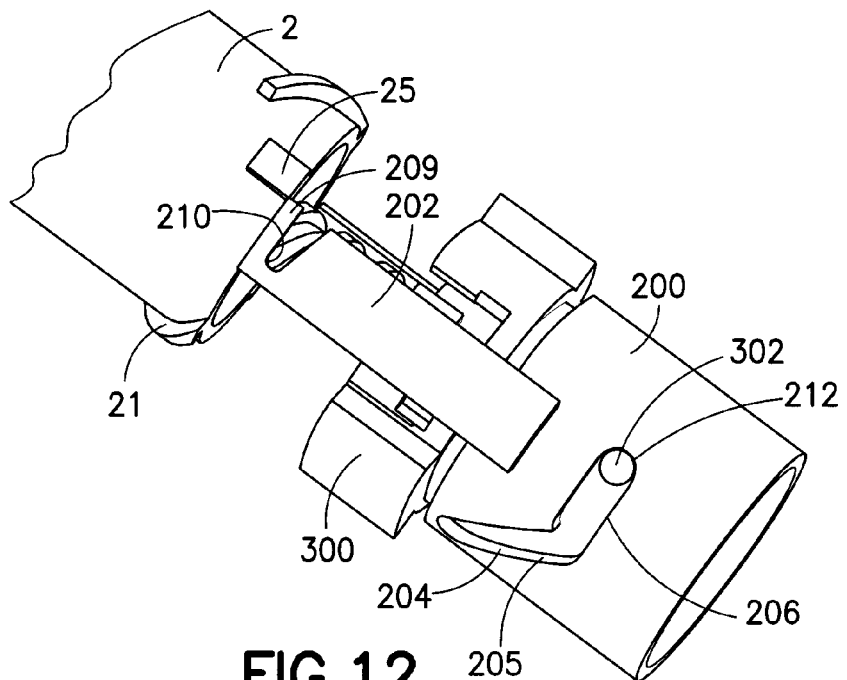
FIG. 12 is a perspective view of the end of injection indicator of FIG. 11 in which the indicator member is fully retracted and disengaged from the lug in the non-visible position.

The indicator member 200 includes at least one arm 202 extending from a cylindrical portion of the indicator member 200 towards the dose set knob 2. A cut-out portion 210 is formed in a proximal end of the arm 202 to form a flexible arm 209 at the proximal end thereof. The arm 202 of the indicator member 200 engages a lug 25 provided adjacent the distal end 56 of the dose set knob 2, as shown in FIG. 10. During setting of a dose, as the dose set knob 2 is rotated, the lug 25 on the dose set knob 2 engages a portion of the arm 202 to cause the indicator member 200 to rotate, as shown in FIG. 11. As the indicator member 200 rotates, the inclined track portion 205 of the indicator member 200 performs a camming function with the boss 302 on the insert 300 such that the indicator member 200 retracts into the body 1 as the boss 302 traverses the inclined track portion 205. As the indicator member 200 retracts, the compression spring 400 compresses between the indicator member 200 and the insert member 300, which is fixed and does not move axially or rotationally. When the boss 302 reaches an end 208 of the inclined track portion 205, the indicator member 200 is fully retracted in the pen body 1 and is not visible to the user, as shown in FIG. 11. The indicator member 200 may further rotate with rotation of the dose set knob 2 until the boss 302 reaches an end of the horizontal track portion 206. As the dose set knob 2 continues to rotate, the lug 25 on the dose set knob 2 moves away from engagement with the arm 202 of the indicator member 200. Eventually the lug 25 on the dose set knob 2 will move far enough that it no longer engages the arm 202 of the indicator 200, as shown in FIG. 12. At this point the indicator 200 no longer rotates and the dose set knob 2 rotates and screws or advances out of the pen upper body 1 a distance corresponding to a set dose, as shown in FIG. 8. The boss 302 is positioned at an end 212 of the horizontal portion 206 of the track 204, as shown in FIG. 12. The boss 302 being disposed in the horizontal portion 206 of the track 204 prevents movement of the indicator member 200 in the distal direction such that the spring 400 (FIG. 9) remains compressed between the indicator member 200 and the insert 300.

During an injection, the dose set knob 2 is screwed back down into the pen upper body 1 upon a user pressing on the button 3 (FIGS. 7 and 8). As the dose set knob 2 nears the end of injection position or the '0' dose position, the dose set knob 2 can reach a position where the lug 25 on the dose set knob 2 engages the top of the arm 202 of the indicator member 200, as shown in FIG. 12. If the lug 25 were to hit the top of the arm 202 instead of passing over the top, it is possible that the pen could jam and the set dose would not be allowed to be completed. Accordingly, the arm 202 on the insert member 200 can include the cutout portion 210 near the top of the arm 202 forming the flexible arm 209. Thus, when the lug 25 contacts the top surface of arm 202, the flexible arm 209 flexes out of the way of the lug 25 so that the dose set knob 2 can continue to its initial position or '0' dose position.

Figure 13:
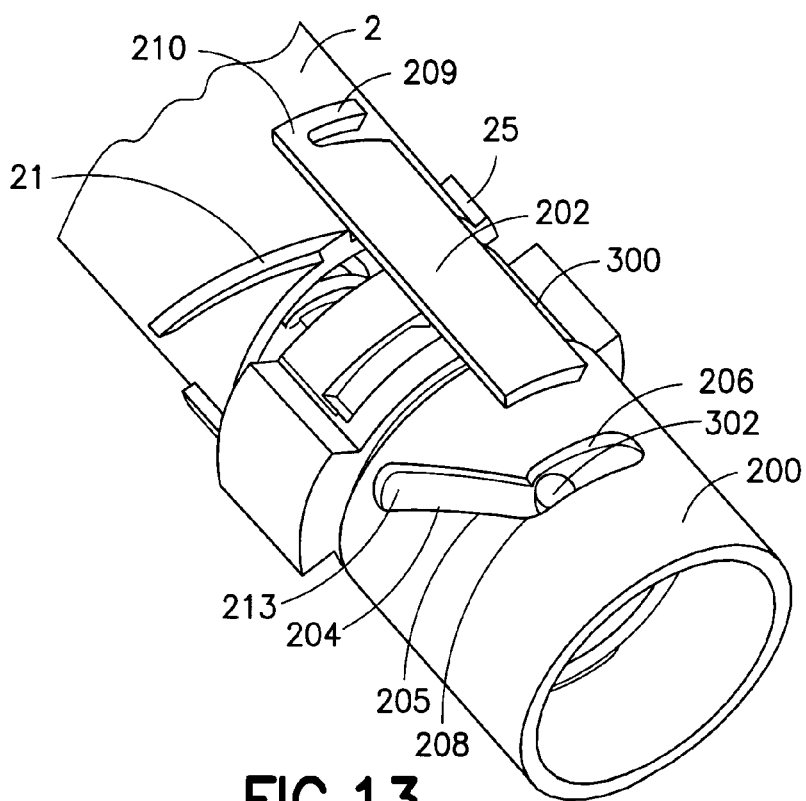
FIG. 13 is a perspective view of the end of injection indicator of FIG. 12 in which the indicator member is engaged by a thread of the dose set knob to release the indicator member to the visible position.

Once the lug 25 passes the arm 202, a thread 21 on the dose set knob 2 contacts a side edge of the arm 202, thus causing rotation of the indicator member 200, as shown in FIG. 13. This interaction preferably occurs just before the dose set knob 2 reaches the '0' dose position. As the indicator member 200 rotates, the horizontal track portion 206 of the track 204 moves over the boss 302 on the insert member 300, as shown. Once the track 204 moves such that the boss 302 is positioned in the inclined track portion 205, the spring 400 (FIG. 9) is released. The spring 400 drives the indicator member 200 in a distal direction away from the insert 300, until the boss 302 is positioned at an end 213 of the inclined track portion 205 of the track 204, as shown in FIG. 10. The end 213 of the track contacting the boss 302 results in a click or snap sound at the end of travel, thereby providing an audible indication that the injection is complete. The critical point when the boss 302 is positioned in the inclined track portion 205 of the track 204 is when the dose set knob 2 has returned to the '0' dose position, such that the injection is completed. The axial movement of the indicator member 200 as the inclined track portion 205 moves over the boss 302 moves the portion of the indicator member 200 into the visible position external of the pen upper body 1, thereby providing the user with a visible indication that the injection is complete.

In a fourth exemplary embodiment shown in FIGS. 14-17, a driver 500 is added to supplement the movement of the indicator member 251. The indicator member 251 is allowed to move an axial distance in and out of the body such that a portion of the indicator member 251 can be visible or exposed to the user in a '0' dose or initial position, but hidden when the dose set knob 2 is not in the '0' dose or initial position, as shown in FIGS. 7 and 8. The indicator member 251 does not rotate, and is limited to axial movement. An insert 271 is fixed to the pen upper body 1, thereby preventing rotational and axial movement of the insert 271. The driver 500 is provided such that it rotates with respect to the pen upper body 1, but does not move axially in and out of the pen upper body 1.

The driver 500 includes a first horizontal track portion 510 that is engaged with a boss 272 on the insert 271 to axially fix the driver 500 to the insert 271 while allowing rotation with respect thereto. Accordingly, the rotational distance over which the dose set knob 2 and an arm 502 of the driver 500 are engaged at the beginning of dose setting and near the end of injection is reduced. Accordingly, any potential for the injection mechanism to jam or fail due to such engagement can be reduced or minimized.

Figure 14:
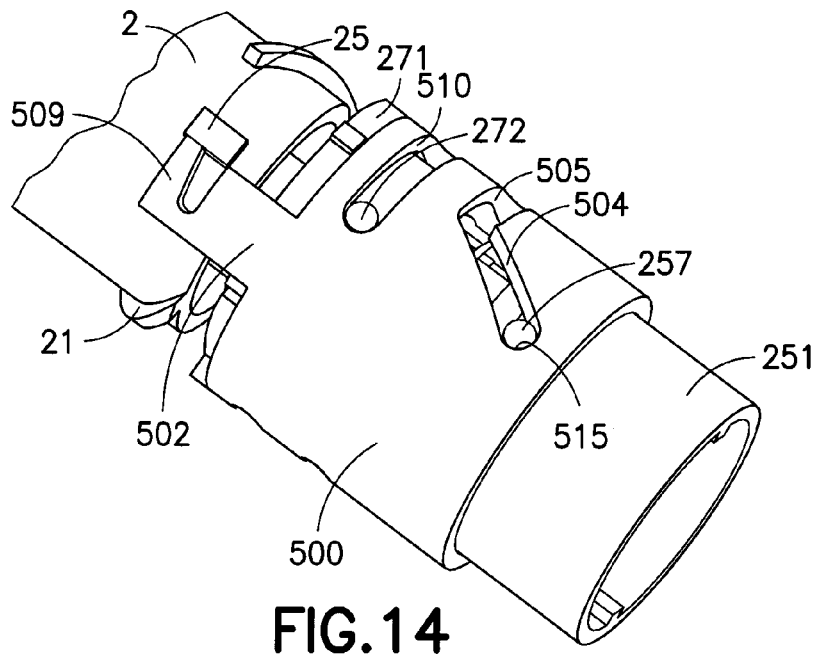
FIG. 14 is a perspective view of an end of injection indicator in accordance with a fourth exemplary embodiment of the present invention in which an indicator member is in a visible position.
Figure 15:
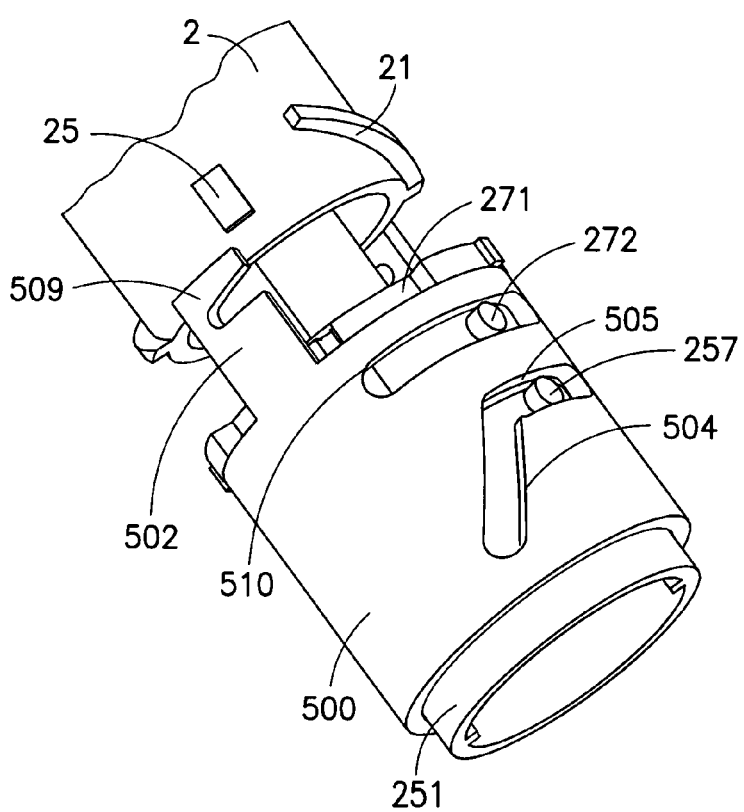
FIG. 15 is a perspective view of the end of injection indicator of FIG. 14 in which a lug of a dose set knob engages a driver to move the indicator member to a non-visible position.

As shown in FIG. 14, the dose set knob 2 is in the '0' dose or initial position, thus an indicator member 251 is visible or exposed to the user. As in the third exemplary embodiment shown in FIGS. 9-13, a spring member (not shown) is provided between the insert 271 and the indicator 251 and is biased to push the indicator member 251 away from the dose set knob 2. As before, when the user adjusts the dose set knob 2 to set a desired dose, the dose set knob 2 is rotated and a lug 25 on the dose set knob 2 engages an arm 502 extending axially from a driver 500. Due to this engagement, the driver 500 is caused to rotate. The driver 500 includes an inclined track portion 504 that engages with a boss 257 provided on the indicator member 251. As the driver 500 rotates, the boss 257 is caused to slide into and up the inclined track portion 504 of the driver 504, thus causing the indicator member 251 to move up into the pen upper body 1 against the bias of the spring member 400 (FIG. 9). The indicator member 251 continues to retract into the pen upper body 1 until the boss 257 reaches the horizontal track portion 505 of the driver 500. At this point, as shown in FIG. 15, the indicator member 251 is completely retracted and the arm 502 is no longer engaged with the lug 25 on the dose set knob 2. Since the arm 502 on the driver 500 does not retract into the pen body with the retraction of the indicator member 251, as in the previous embodiment, the arm 502 and the dose set knob 2 are engaged for a shorter period of time and over a shorter rotational distance. The boss 257 being positioned in the horizontal track portion 505 maintains the spring member in the compressed position.

Figure 16:
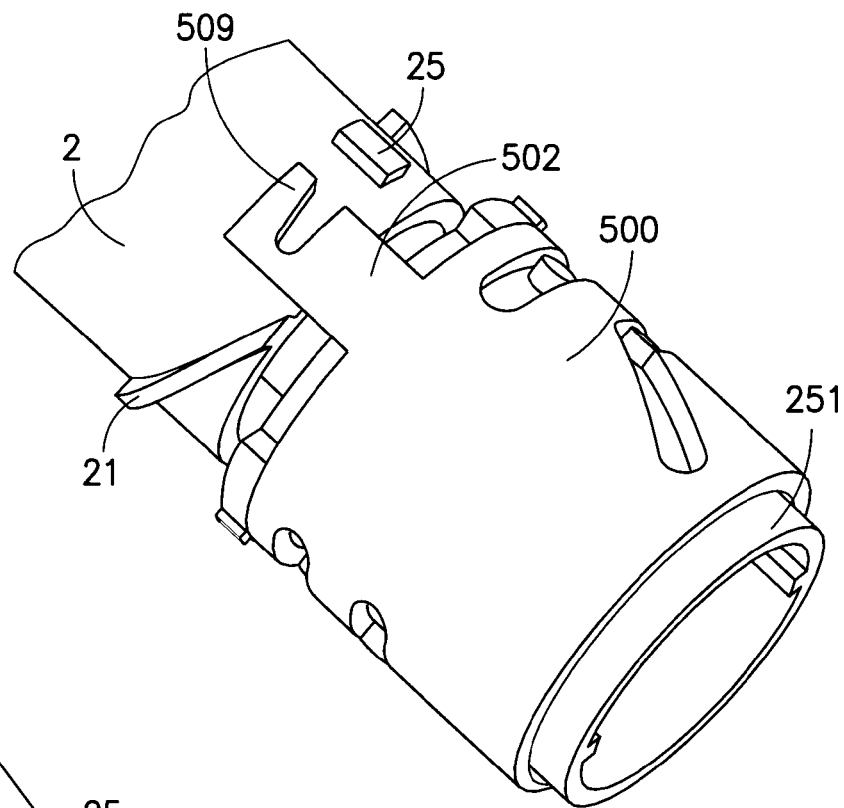
FIG. 16 is a perspective view of the lug of the dose set knob disengaged from the driver.
Figure 17:
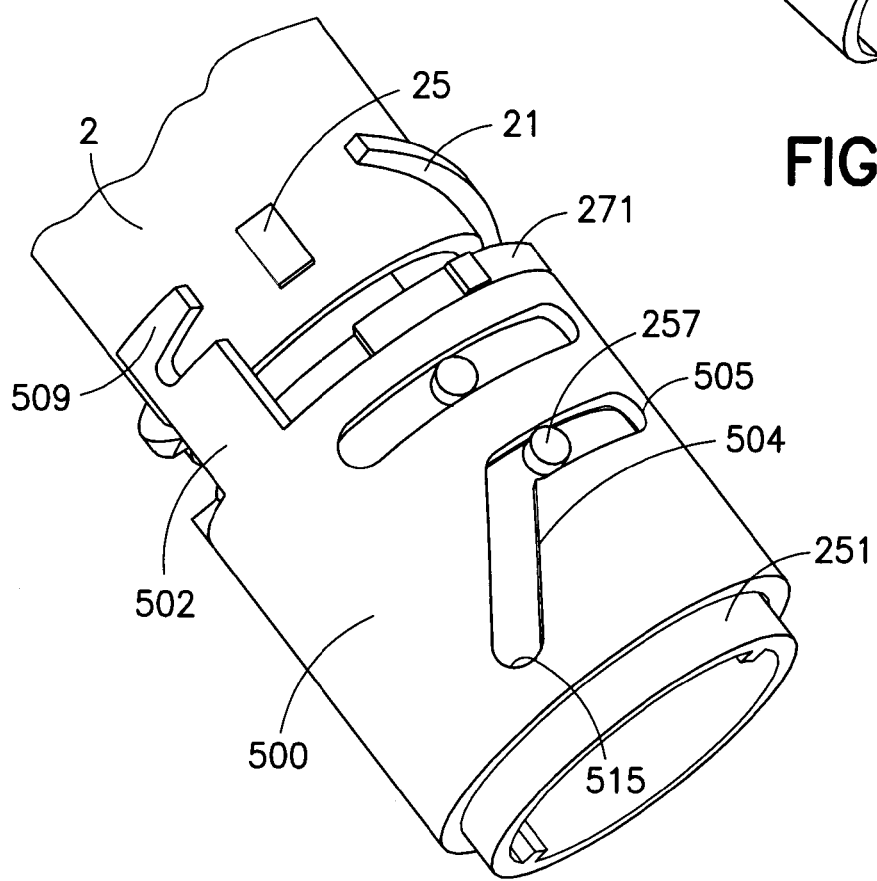
FIG. 17 is a perspective view of a thread of the dose set knob engaging the driver to move the indicator member to the visible position.

During injection, the dose set knob 2 moves back toward its '0' dose or initial position toward arm 502 of the driver element 500. When the lug 25 engages with a top edge of the arm 502 during return of the dose set knob 2, a flexible arm 509 of the driver arm 502 flexes downwardly such that the lug 25 can move past the arm 502 of the driver 500. The driver 500 rotates upon engagement of a thread 21 on the dose set knob 2 with the side edge of the arm 502, as shown in FIG. 16. As the driver 500 rotates, the boss 257 moves in the horizontal portion of track 505, as shown in FIG. 17, until it reaches the inclined track portion 504. At this point, the spring element 400 (FIG. 9) disposed between the insert 271 and the indicator member 251 is released and pushes the indicator member 251 away from the dose set knob 2 and out of the pen upper body 1 such that it is visible to the user. Once again, when the boss 257 reaches an end 515 of the inclined track portion 504, as shown in FIG. 14, an audible and/or tactile click or snap is generated.

Figure 18:
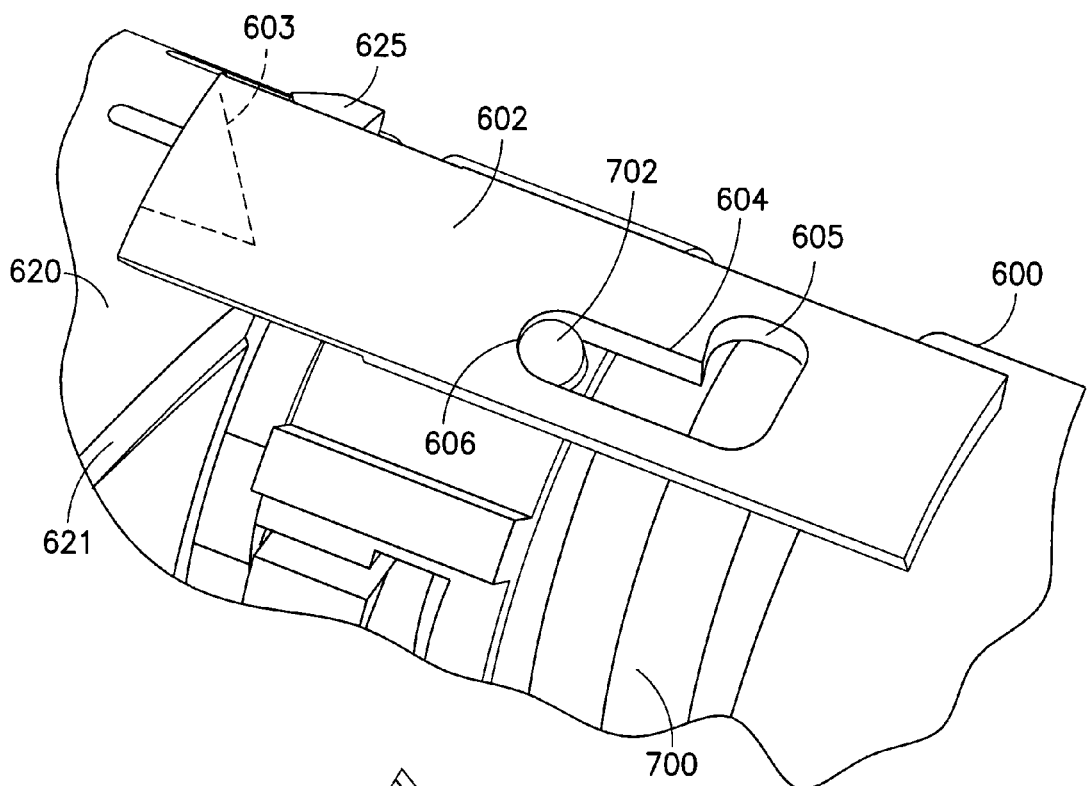
FIG. 18 is a perspective view of an end of injection indicator according to a fifth exemplary embodiment of the present invention in which an indicator member is in a visible position.
Figure 19:
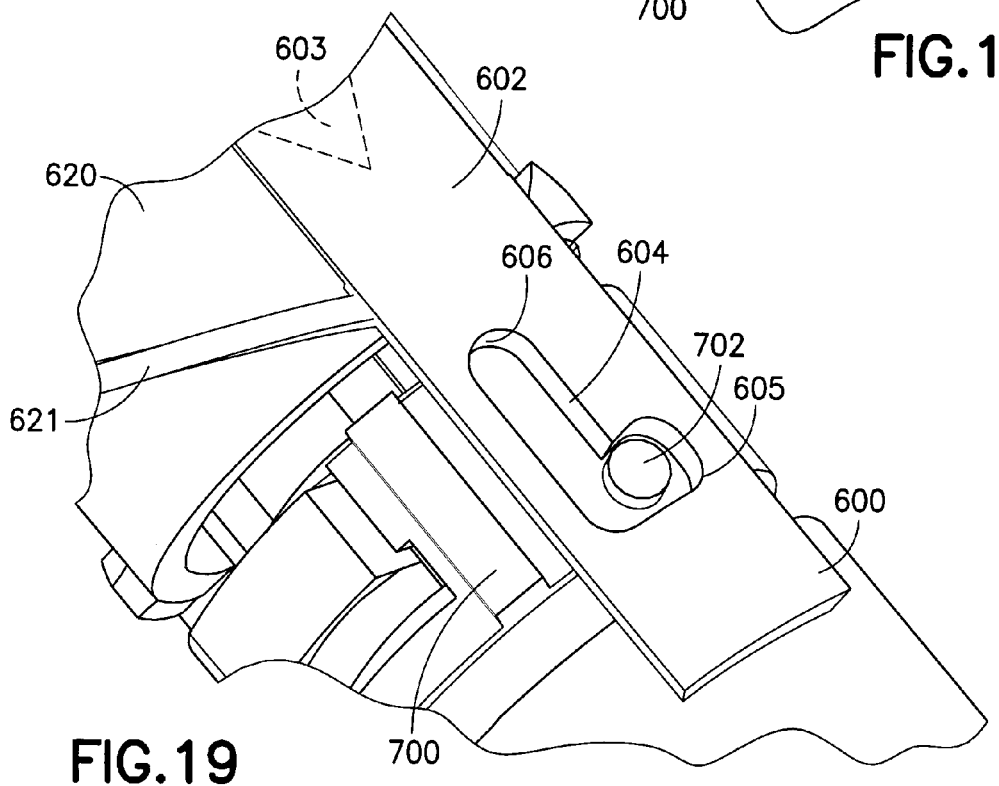
FIG. 19 is a perspective view of the end of injection indicator of FIG. 18 with the indicator member in a non-visible position.

FIGS. 18 and 19 illustrate a fifth exemplary embodiment of an end of injection indicator. A generally cylindrical indicator member 600 surrounds an insert member 700 to provide an indication that the dose set knob 620 has returned to its '0' dose or initial position similar to the above exemplary embodiments. The indicator member 600 includes an at least one elongate arm 602 that engages the dose set knob 620. The dose set knob 620 in this exemplary embodiment includes an angled lug 625 that engages a corresponding angled portion 603 on the internal surface of the arm 602 to lift the indicator member 600 upon rotation of the dose set knob 620. As the dose set knob 620 is rotated to set a dose, the indicator member 600 is lifted or pulled into the pen upper body 1, against the bias of a spring member 400 (FIG. 9) disposed between the insert 700 and the indicator member 600. The indicator member 600 is moved axially into the upper pen body 1 a distance corresponding to the length of a vertical track portion 604 of the indicator member. The indictor member 600 is lifted by the engagement with the lug 625 on the dose set knob 620 just enough for a boss 702 on an insert member 700 to traverse the length of the vertical track portion 604 and move into the horizontal portion 605, as shown in FIG. 19, that secures the indicator member 600 in the retracted position until the dose set knob 620 returns to the '0' dose or initial position. The spring member 400 (FIG. 9) remains compressed when the boss 702 is disposed in the horizontal track portion 605 and prevents axial movement of the indicator member 600.

FIG. 19 illustrates the indicator member 600 just before the dose set knob 620 returns to the '0' dose or initial position. As shown, just before the dose set knob 620 reaches the '0' dose or initial position, a thread 621 on the dose set knob 620 engages an edge of the arm 602 to cause the arm 602 to rotate a slight amount that will release the boss 702 disposed on the insert 700 from the horizontal track portion 605 into the vertical track portion 604. Once the boss 702 is aligned in the vertical track portion 604, the spring member 400 (FIG. 9) releases and pushes the indicator member 600 away from the dose set knob 620, such that a portion of the indicator member 600 is exposed outside the pen upper body 1 similar to the above exemplary embodiments to be visible to the user. As before, when the boss 702 reaches an end 606 of the vertical track portion 604, an audible and/or tactile click or snap is generated.

Figure 20:
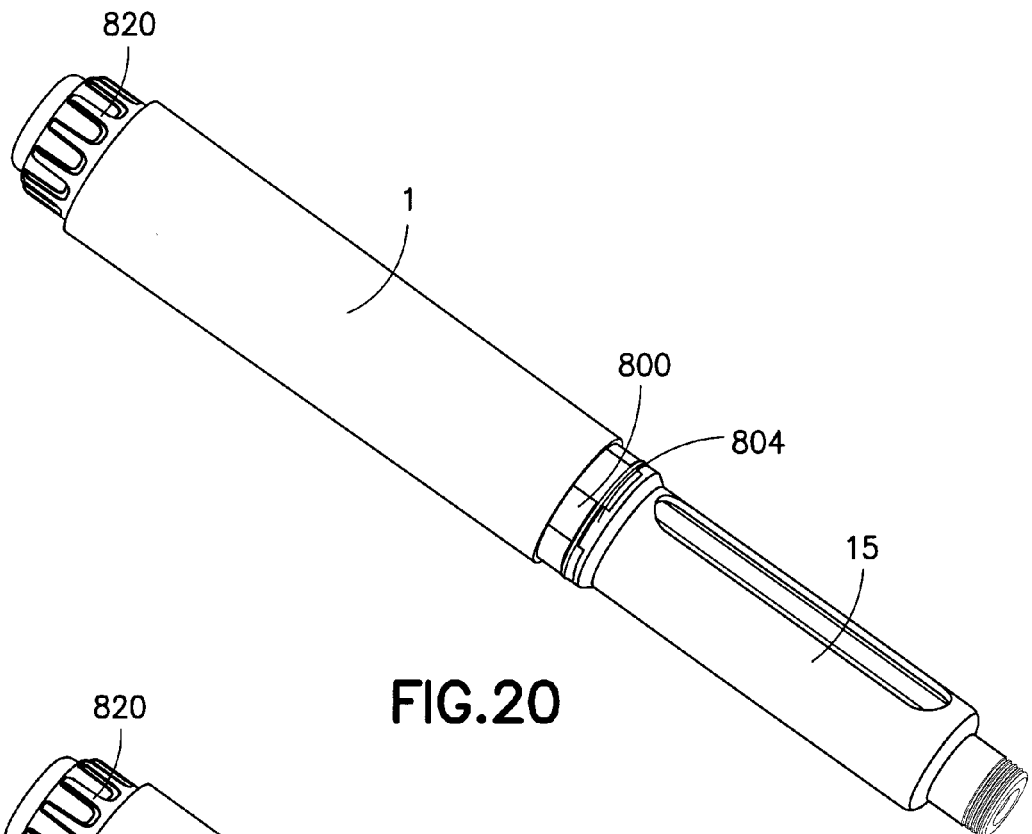
FIG. 20 is a perspective view of an injection pen having an end of injection indicator in accordance with a sixth exemplary embodiment of the present invention with the indicator member shown in the visible position.
Figure 22:
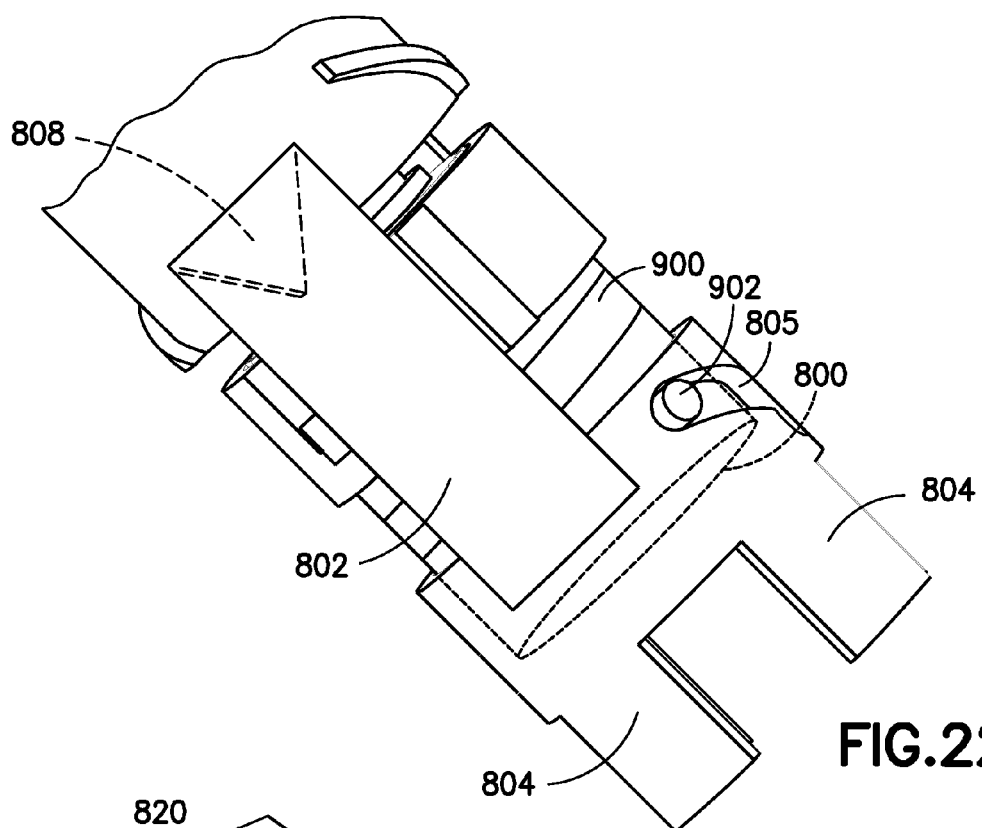
FIG. 22 is a perspective view of the indicator member of FIG. 20 in the visible position.

According to a sixth exemplary embodiment shown in FIGS. 20-23, instead of pushing an indicator out from the pen upper body 1 such that it is exposed or visible to a user, an indicator 800 is configured to rotate such that a portion of indicator 800 is visible to the user. As shown in FIG. 22, an indicator member 800 includes a plurality of legs 804 that are circumferentially spaced apart. Thus, as the indicator member 800 rotates relative to the pen upper body 1, one of the legs 804 rotates into a view of the user, as shown in FIG. 20. FIG. 22 illustrates this embodiment when the dose set knob 2 is rotated an amount to set a dose, such that the dose set knob 2 is no longer in the '0' dose or initial position. As shown, none of the legs 804 of the indictor member 800 are visible to the user. Instead, a portion of the cartridge holder 15 may be visible.

Figure 23:
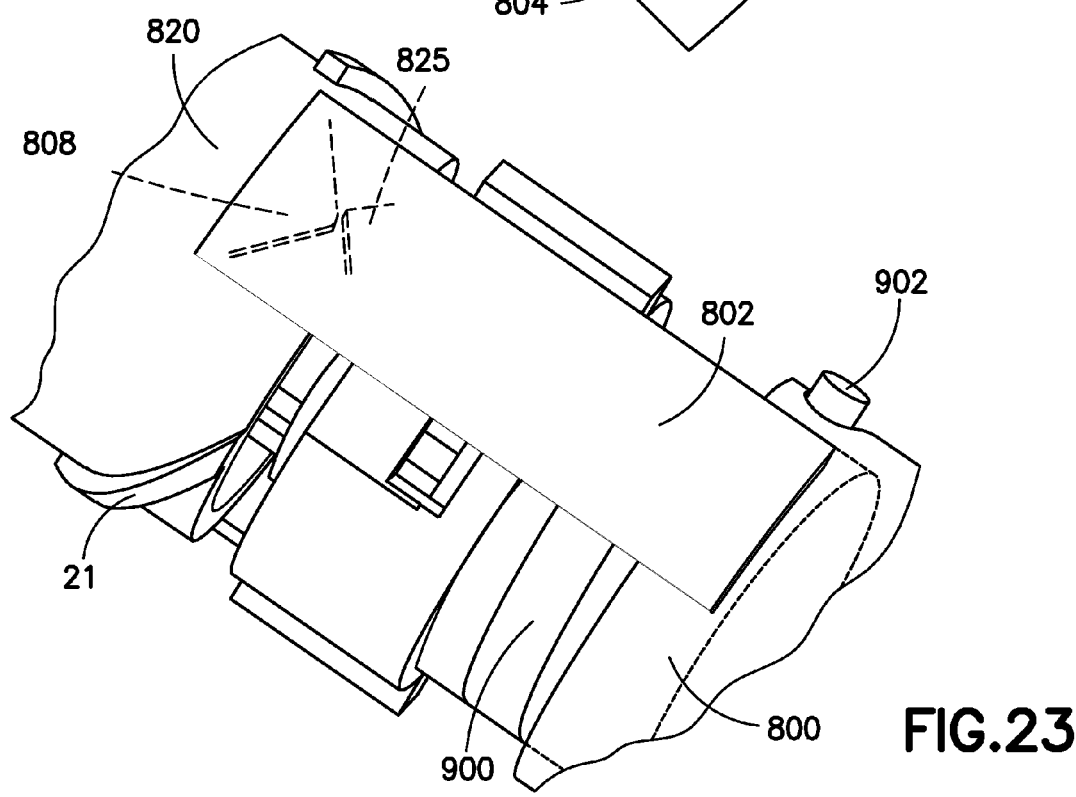
FIG. 23 is a perspective view of the indicator member of FIG. 20 in the non-visible position.

One difference between the embodiment of FIGS. 20-23 and the previous embodiments is that a torsion spring is provided between an insert 900 and the indicator member 800 instead of a compression spring. As shown in FIG. 22, the indicator member 800 includes a track 805 that engages with a boss 902 provided on the insert member 900. At least one arm 802 extends from the indicator member toward and engages the dose set knob 820. The dose set knob 820 is provided with an angled lug 825, as shown in FIG. 23, that engages with a similar angled member 808 provided on the internal surface of arm 802. As the dose set knob 820 is rotated to set a desired dose, engagement between the angled portions 825 and 808 causes the indicator member 800 to lift or move into the pen upper body 1 a small amount and rotate against the bias of the torsion spring to move the boss 902 disposed on the insert 900 into a secured position, not shown, within the track 805. The boss 902 is held in the secured position against the bias of the torsion spring until the arm 802 is engaged near the '0' dose or initial position by the dose set knob 820. Once the dose set knob 820 engages the arm 802 during its return, the indicator member 800 is rotated an amount that releases the boss 902 such that the torsion spring causes the indicator member 800 to rotate back. Once the indicator member 800 rotates back with the force of the torsion spring, one of the legs 804 are visible to a user to indicate that the dose set knob 820 is in the '0' dose or initial position. Return of the boss 902 in the track 805 under the force of the spring member results in an audible and/or tactile click or snap perceivable to the user.

Figure 24:
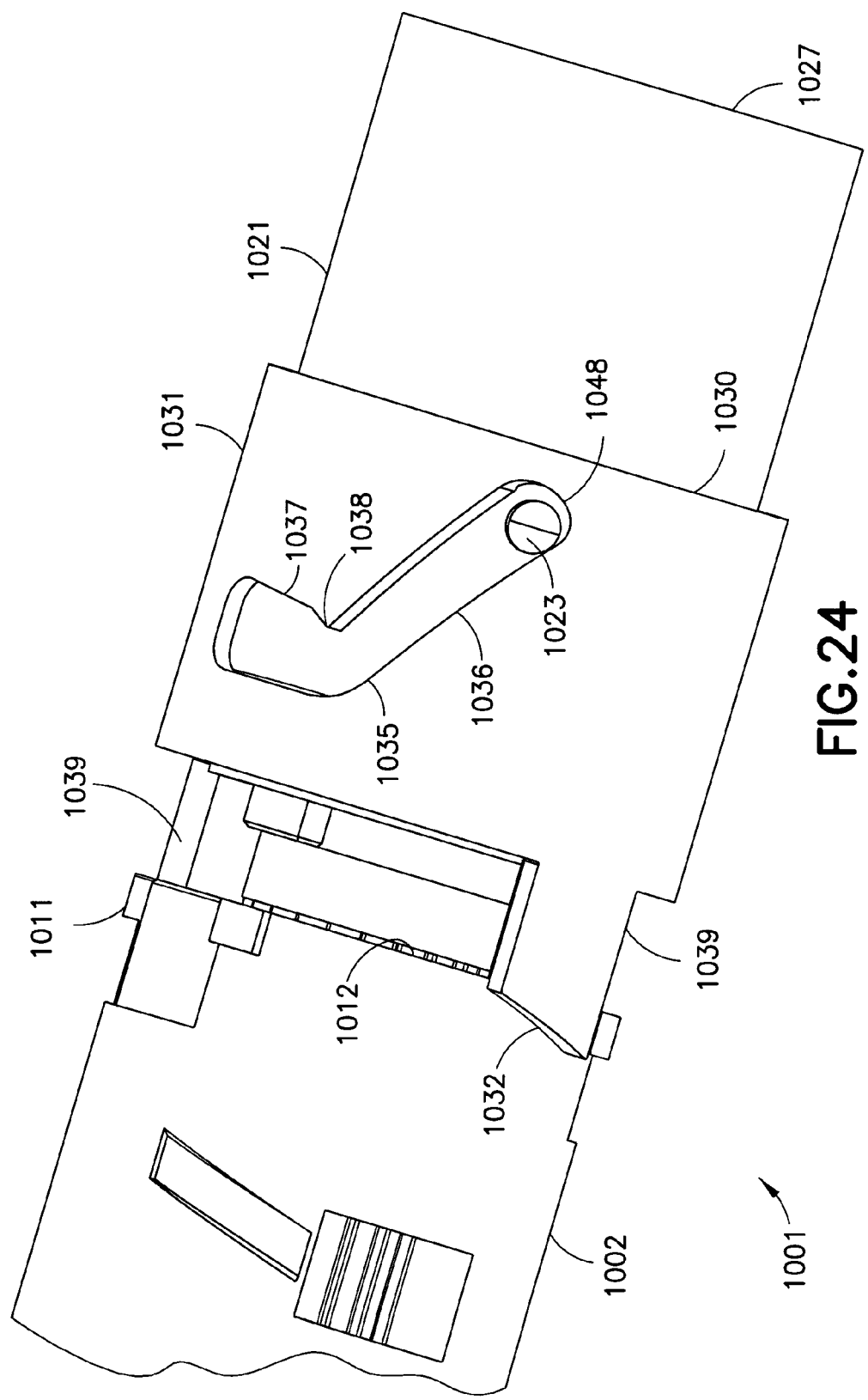
FIG. 24 is a perspective view of an injection indicator according to a seventh exemplary embodiment of the present invention with the indicator shown in a visible position.
Figure 25:
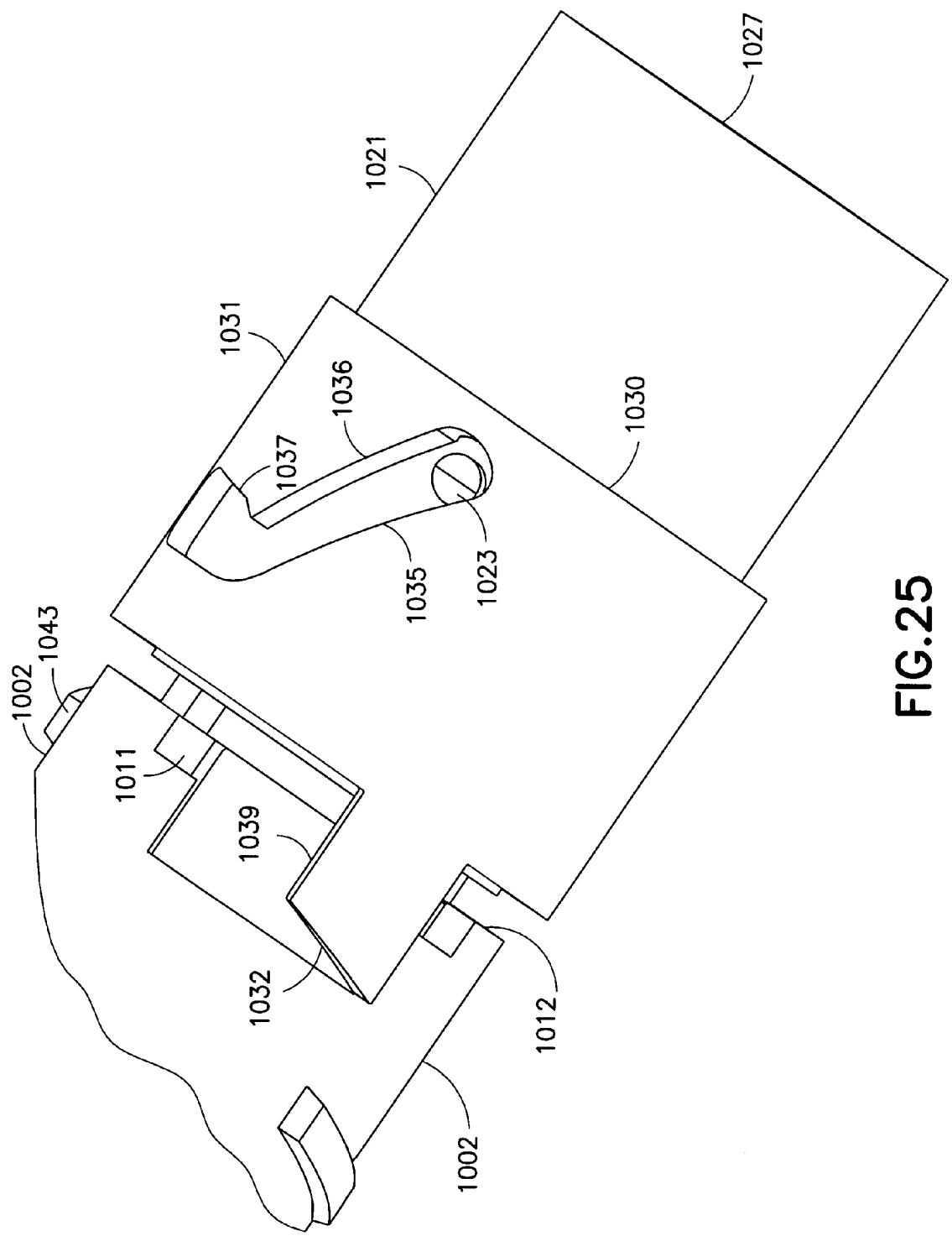
FIG. 25 is another perspective view of the injection indicator of FIG. 24 with the indicator member shown in the visible position.
Figure 29:
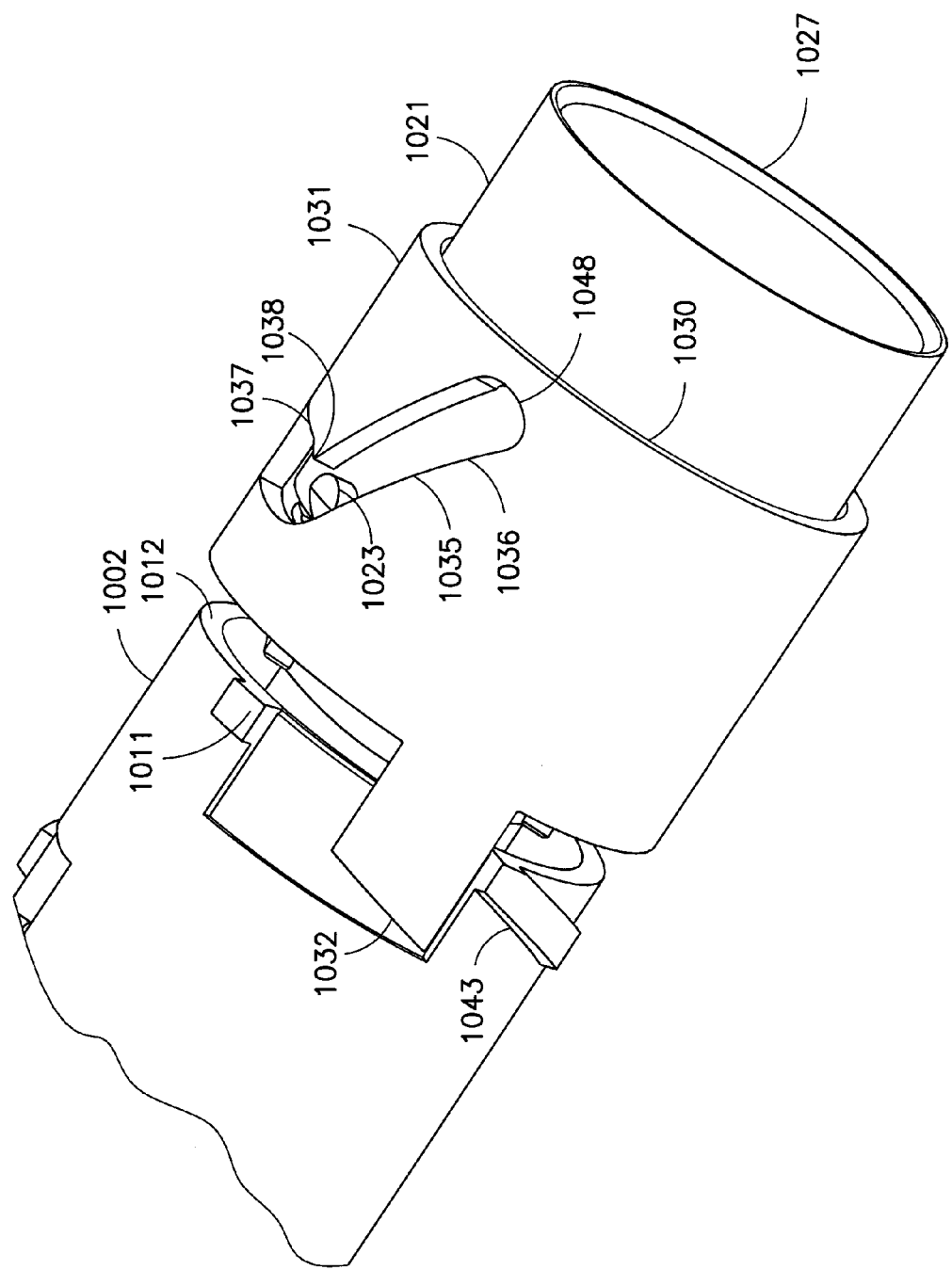
FIG. 29 is a perspective view of the injection indicator of FIG. 24 with the indicator member being engaged by a dose set know thread.
Figure 30:
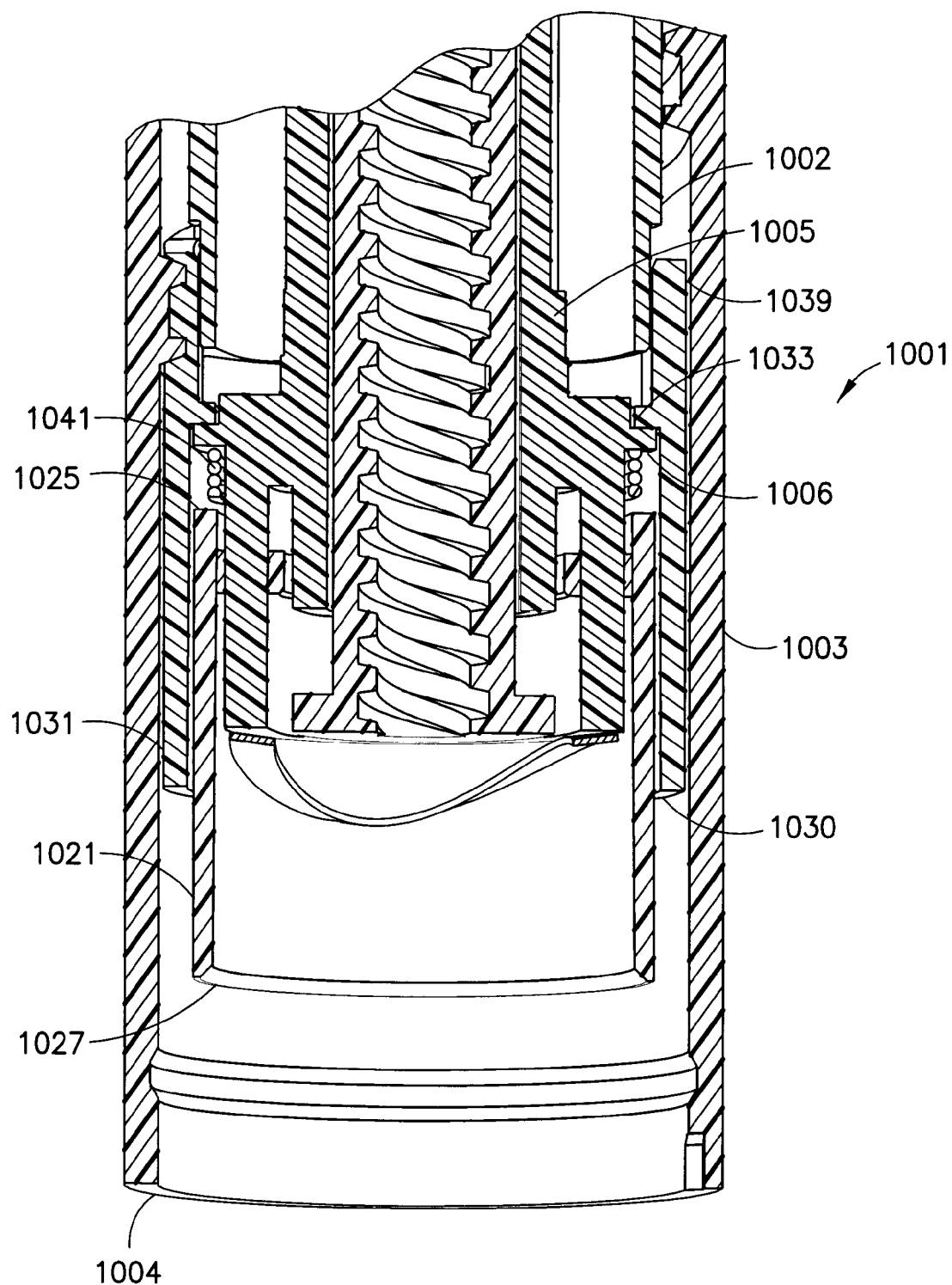
FIG. 30 is a partial elevational view in cross-section of an injection pen including the injection indicator of FIG. 24 in the non-visible position.
Figure 31:
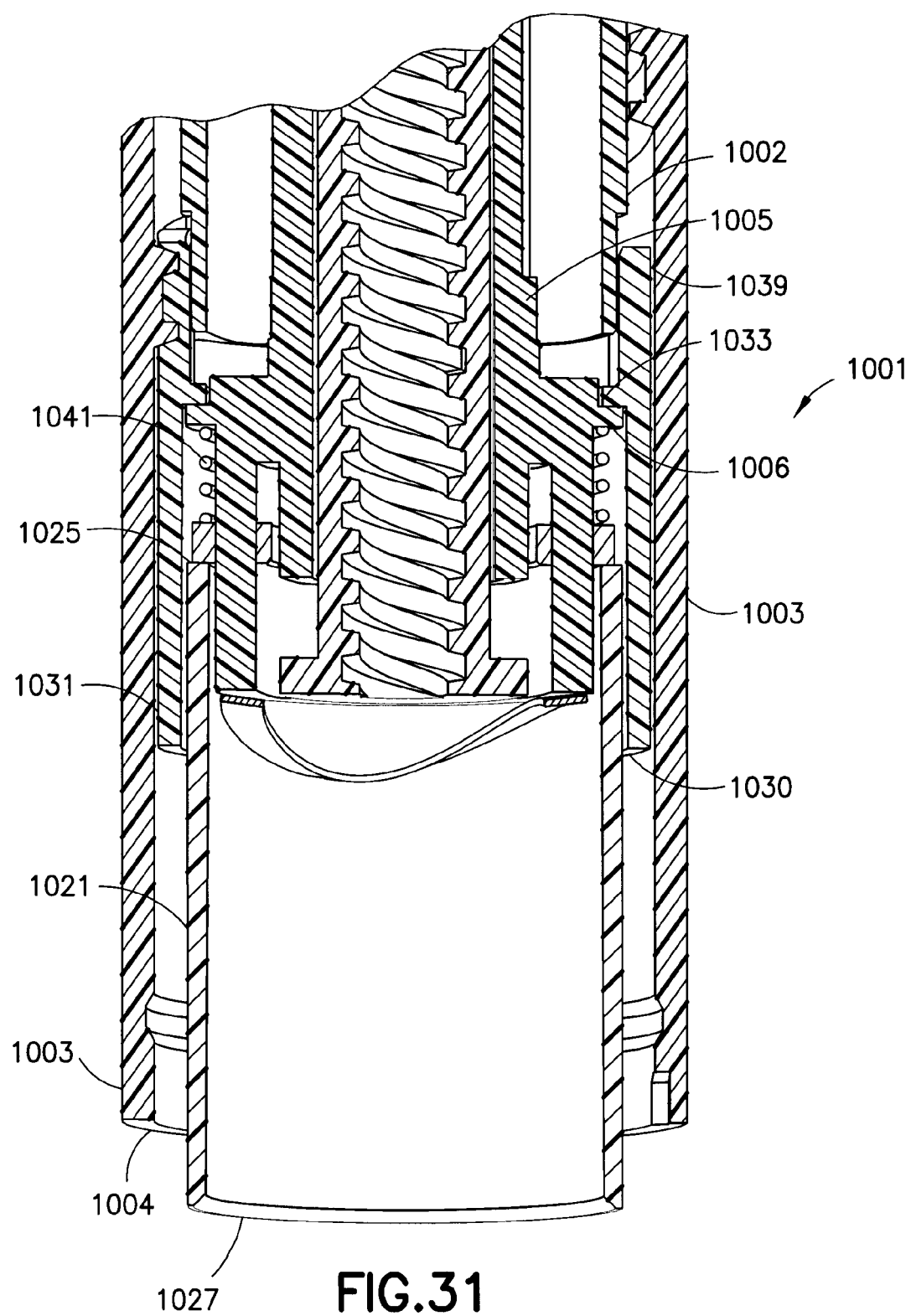
FIG. 31 is a partial elevational view in cross-section of the injection pen of FIG. 30 with the indicator member in the visible position.

An end of injection indicator according to a seventh exemplary embodiment of the present invention is shown in FIGS. 24-31. An indicator member 1021 is in the visible or exposed position and is visible only when the dose set knob 1002 is in the '0' dose or initial position as shown in FIGS. 24 and 25. Accordingly, as shown in FIGS. 26-29, when the dose set knob 1002 is not in its initial position (for example, as shown by the gap 'a' between the dose set knob 2 and the pen upper body 1 in FIG. 8), the indicator member 1021 is no longer in the visible position. The exposed indicator member 1021 is more readily visible to the user when the dose set knob 1002 is in its initial or end of injection position due to the indicator member 200 extending beyond a distal end 1004 of a pen upper body 1003, as shown in FIG. 31. The cartridge housing 15 (FIGS. 7 and 8, for example) is preferably transparent or translucent to facilitate visibility of the indicator member 1021 in the visible position.

The energy used to activate the indicator member 1021 of FIGS. 24-31 is stored during the dose setting action performed by the user. To facilitate the injection process, the force required to release the indicator member 1021 to the visible position is preferably minimal and unnoticeable to the user. A cross-section of an end of injection mechanism to expose the indicator member 1021 is shown in FIGS. 30 and 31. Operation of the injection mechanism is shown in FIGS. 24-29, in which the pen body 1003 and the cartridge holder 15 (FIGS. 7 and 8) are removed to more clearly illustrate the operation thereof.

As shown in FIGS. 24-29, the indicator member 1021 is of a substantially cylindrical shape and is coaxially surrounded by an insert 1031. The insert 1031 is prevented from moving axially in the distal direction by and outwardly extending flange 1005 of the brake tower 1005 receiving an inwardly extending shoulder 1033 of the insert 1031. Axial movement in the proximal direction and rotational movement with respect to the pen upper body 1003 is substantially prevented by a boss 1023 of the indicator member 1021 received in a track 1035 of the insert 1031. A spring member 1041 is disposed between the flange 1005 of the brake tower 1005 and a proximal end 1025 of the indicator member 1021, as shown in FIGS. 30 and 31. The spring member 1041 biases the indicator member 1021 to the visible position shown in FIGS. 24 and 25, and prevents movement of the indicator member 1021 and the insert 1031 due to the boss 1023 and track 1035 connection therebetween.

FIGS. 24 and 25 depict the indicator member 1021 in the visible or exposed position, such that a portion of the indicator member 1021 is visible to the user through the transparent or translucent cartridge housing 15 (FIGS. 7 and 8). As such, the dose set knob 1002 is in its initial or '0' dose position. A portion of the indicator member 1031 at a distal end 1027 thereof is visible beyond the distal end 1004 of the pen upper body 1003 when the indicator member 1021 is in the visible position.

Figure 26:
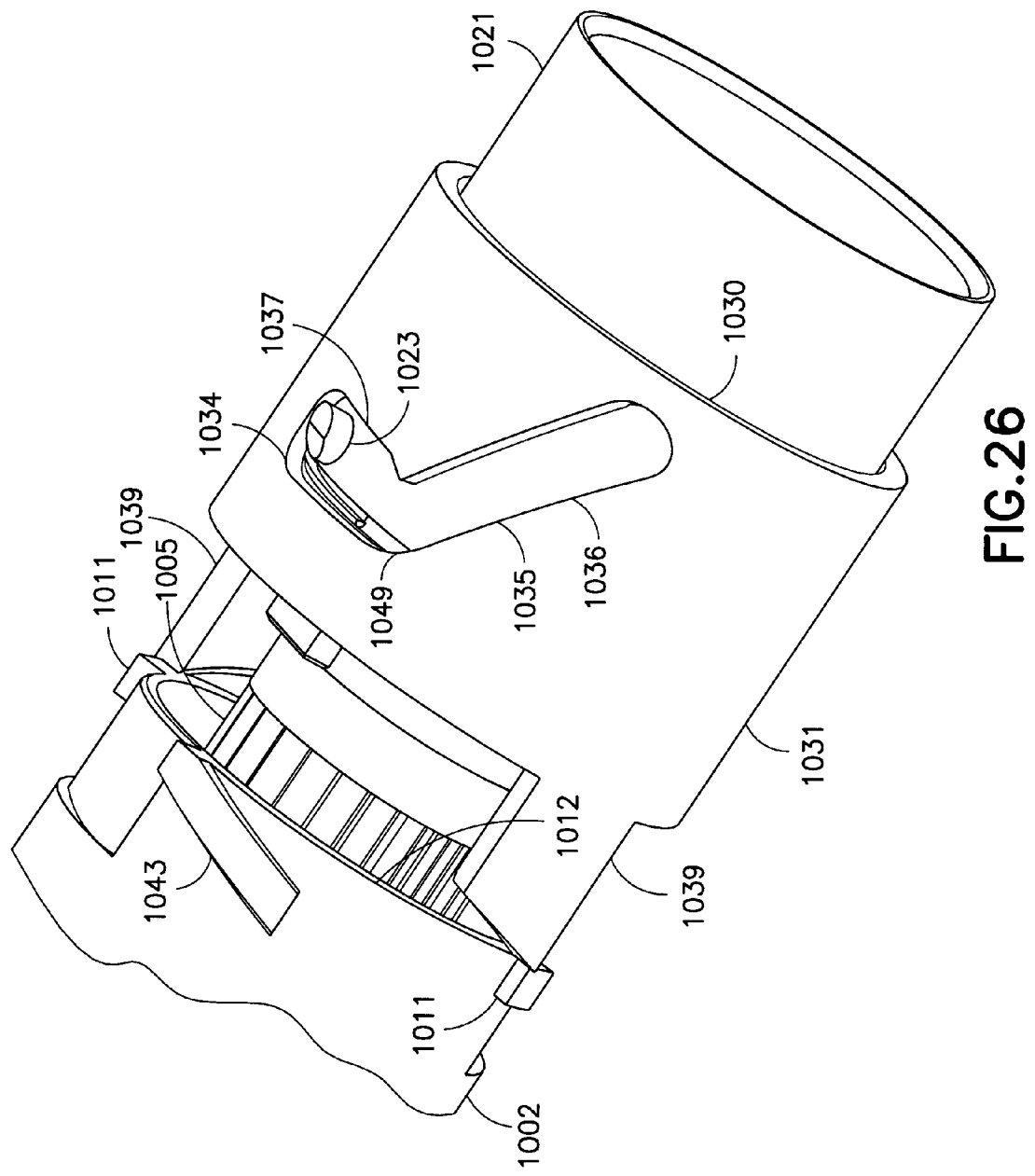
FIG. 26 is a perspective view of the injection indicator of FIG. 24 with the indicator member shown in the non-visible position.
Figure 27:
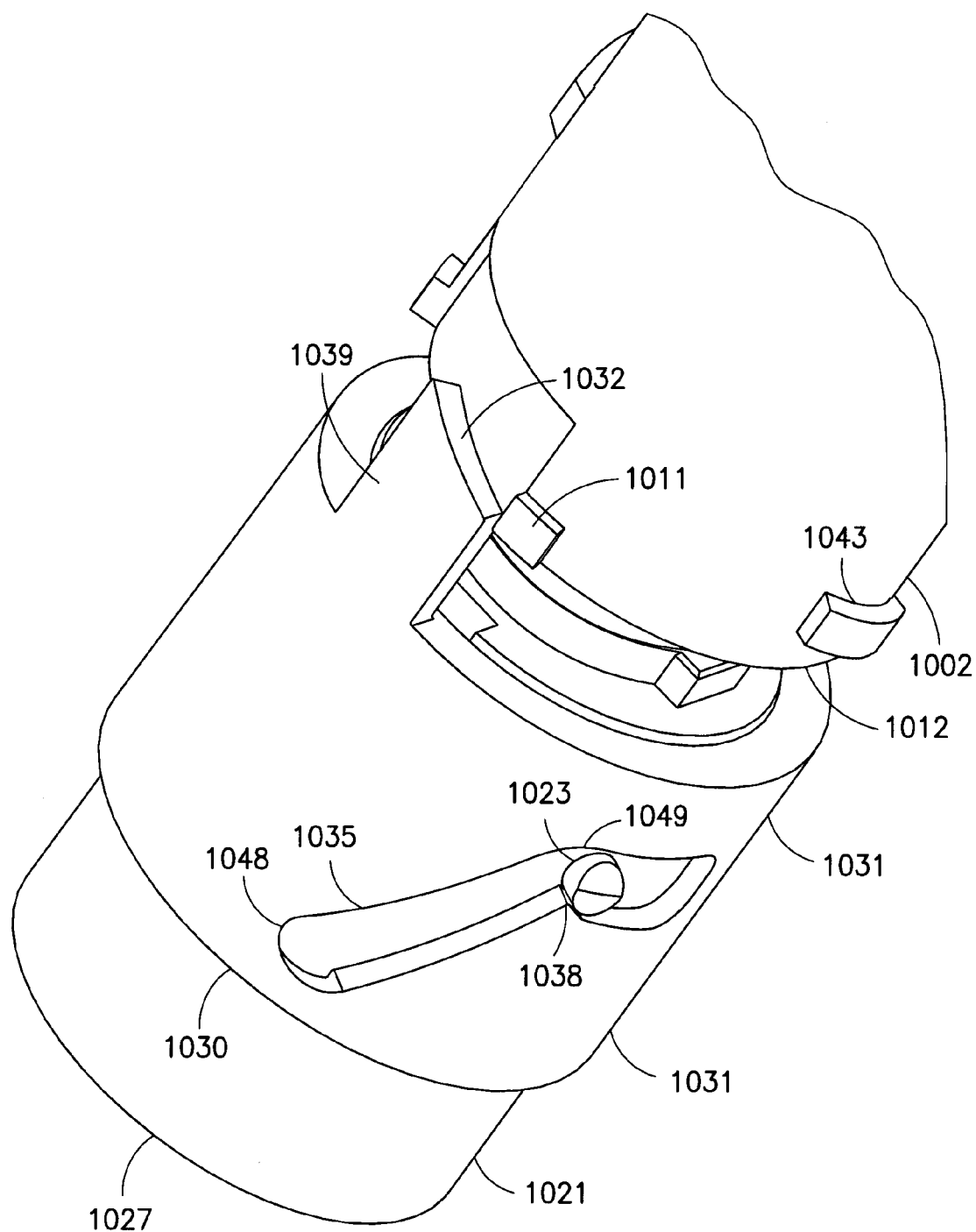
FIG. 27 is another perspective view of the injection indicator of FIG. 24 with the indicator member shown in the non-visible position.
Figure 28:
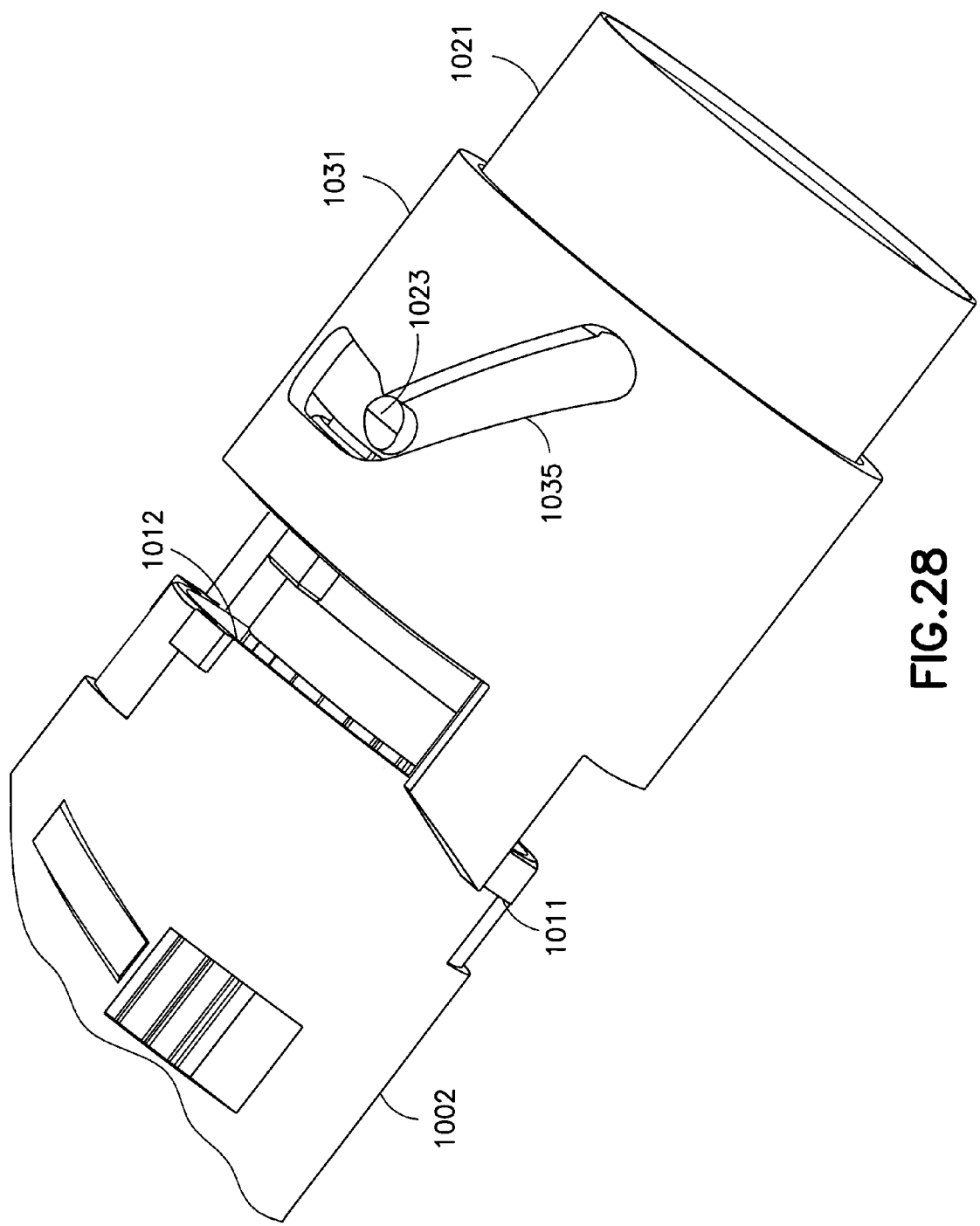
FIG. 28 is a perspective view of the injection indicator of FIG. 24 with the indicator member moving from the non-visible position to the visible position.

As shown in FIGS. 24-29, the track 1035 has a first or inclined portion 1036 extending in a distal direction at an angle to the longitudinal axis of the pen upper body 1003 (FIGS. 30 and 31). A second or horizontal portion 1037 of the track 1035 extends substantially perpendicular to the longitudinal axis of the pen upper body 1003 (FIGS. 30 and 31) from an end of the first portion 1036 of the track 1035. A ramp 1038 is formed at the transition from the second portion 1037 to the first portion 1036 of the track 1035 to maintain the boss 1023 in the second portion 1037 of the track 1035 when the dose set knob 1002 is in a non-zero position, as shown in FIGS. 26 and 27.

The insert 1031 includes at least one arm 1039 extending from a cylindrical portion of the insert 1031 towards the dose set knob 1002, as shown in FIGS. 24-31. A distal end 1032 of the arm 1039 slopes downwardly toward the distal end of the pen 1001 (FIGS. 30 and 31). The arm 1039 of the insert 1031 engages a lug 1011 provided adjacent a distal end 1012 of the dose set knob 1002. During setting of a dose, as the dose set knob 1002 is rotated, the lug 1011 on the dose set knob 1002 engages a portion of the arm 1039 to cause the insert 1031 to rotate, as shown in FIGS. 25 and 26. As the insert 1031 rotates, the inclined track portion 1036 of the insert 1031 performs a camming function with the boss 1023 on the indicator member 1021 such that the indicator member 1021 retracts into the body 1003 as the boss 1023 traverses the inclined track portion 1036. As the indicator member 1021 retracts, the spring member 1041 compresses between the indicator member 1021 and the flange 1006 of the brake tower 1005, which is fixed to the pen upper body 1003 and does not move axially or rotationally. When the boss 1023 reaches an end 1049 of the inclined track portion 1036, the indicator member 1021 is fully retracted in the pen body 1003 and is not visible to the user, as shown in FIGS. 26 and 27. The indicator member 1021 further rotates with rotation of the dose set knob 1002 until the boss 1023 reaches an end of the horizontal track portion 1037. As the dose set knob 1002 continues to rotate, the lug 1011 on the dose set knob 1002 moves away from engagement with the arm 1039 of the insert 1031. Eventually the lug 1011 on the dose set knob 1002 moves far enough that it no longer engages the arm 1039 of the insert 1031, as shown in FIG. 26. At this point the insert 1031 no longer rotates and the dose set knob 1002 rotates and screws or advances out of the pen upper body 1003 a distance corresponding to a set dose, as shown in FIG. 8. The boss 1023 is positioned at an end 1034 of the horizontal portion 1037 of the track 1035, as shown in FIGS. 26 and 27. The boss 1023 being disposed in the horizontal portion 1037 of the track 1035 prevents movement of the indicator member 1021 in the distal direction such that the spring 1041 remains compressed between the indicator member 1021 and the flange 1006 of the brake tower 1005.

During an injection, the dose set knob 1002 is screwed back down or advanced into the pen upper body 1003 upon the user pressing on the button 3 (FIGS. 7 and 8). As the dose set knob 1002 nears the end of injection position or the '0' dose position, the dose set knob 1002 can reach a position where the lug 1011 on the dose set knob 1002 engages the top of the arm 1039 of the insert 1031. If the lug 1011 were to hit the top of the arm 1039 instead of passing over the top, it is possible that the pen could jam and the set dose would not be allowed to be completed. Accordingly, the arm 1039 on the insert 1031 is sloped downwardly toward a distal end 1030 of the insert 1031. Thus, when the lug 1011 contacts the top surface of the arm 1039, the sloped proximal end of the arm 1039 facilitates the lug 1011 passing over the arm 1039 so that the dose set knob 1002 can continue to its initial position or '0' dose position.

Once the lug 1011 passes the arm 1039, a thread 1043 on the dose set knob 2 contacts a side edge of the arm 1039, thus causing rotation of the insert 1031, as shown in FIG. 29. This interaction preferably occurs just before the dose set knob 1002 reaches the '0' dose position. As the insert 1031 rotates, the boss 1023 moves in the horizontal track portion 1037 on the insert 1031. Once the insert 1031 rotates such that the boss 1023 is positioned at the ramp 1038 in the track 1035 and the arm 1039 is positioned at the second end 1063 of the recess 1061 in the dose set knob 1002. Continued rotation of the dose set knob 1002 forces the boss 1023 to pass over the ramp 1038 of the track 1035 in the insert 1031. When the boss 1023 passes the ramp 1038, the spring 1041 is released. The spring 1041 drives the indicator member 1021 in a distal direction away from the insert 1031, until the boss 1023 is positioned at an end 1048 of the inclined track portion 1036 of the track 1035, as shown in FIGS. 24 and 25. The end 1048 of the track 1035 contacting the boss 1023 results in a click or snap sound at the end of travel, thereby providing an audible indication that the injection is complete. The critical point when the boss 1023 is positioned in the inclined track portion 1036 of the track 1035 is when the dose set knob 1002 has returned to the '0' dose position, such that the injection is completed. The axial movement of the indicator member 1021 as the boss moves in the inclined track portion 1036 moves the portion of the indicator member 1021 into the visible position external of the pen upper body 1003, as shown in FIG. 31, thereby providing the user with a visible indication that the injection is complete.

The injection pens described herein may utilize conventional dose setting and injection mechanisms as disclosed, for example, in U.S. Pat. Nos. 5,626,566, 6,235,004, and 7,241,278, all of which are hereby incorporated by reference in their entirety.

While the present invention has been shown and described with reference to particular illustrative embodiments, it is not to be restricted by such exemplary embodiments. It is to be appreciated that those skilled in the art can change or modify the exemplary embodiments without departing from and the scope and spirit of the present invention as defined in the appended claims and their equivalents.

The invention claimed is:
1. A medication injection pen, comprising:
a housing having a proximal end and a distal end;
a dose set knob extending from said proximal end and rotatably connected to said housing for setting a dose;
a plurality of numerals corresponding to a set dose;
an indicator member positioned distally of the plurality of numerals and movable between a visible position indicating a zero position of said dose set knob and a non-visible position indicating a non-zero position of said dose set knob, said dose set knob being in said zero position when a set dose has been completely administered, wherein
the indicator member is visible in the visible position and not visible in the non-visible position.
2. The medication injection pen according to claim 1, wherein
a spring member biases said indicator member to said zero position.
3. The medication injection pen according to claim 1, wherein
an arm extends axially from said indicator member toward said dose set knob.
4. The medication injection pen according to claim 3, wherein
a lug disposed on said dose set knob engages said arm when rotating said dose set knob to set a dose to move said indicator member from said visible position to said non-visible position.
5. The medication injection pen according to claim 4, wherein a thread disposed on said dose set knob engages said arm when injecting a set dose to move said indicator member from said non-visible position to said visible position.

6. The medication injection pen according to claim 5, wherein
a flexible arm is disposed at an end of said arm to allow said lug to pass over said arm when injecting said set dose.

7. The medication injection pen according to claim 2, wherein
an insert is fixed to said housing and has a boss extending outwardly therefrom; and
a track in said indicator member receives said boss to guide said indicator member between said visible position and said non-visible position.

8. The medication injection pen according to claim 7, wherein
said track has a first portion and a second portion, such that movement of said boss through said first portion provides axial movement of said indicator member and movement of said boss through said second portion prevents axial movement of said indicator member.

9. The medication injection pen according to claim 7, wherein
said spring moves said indicator member to said visible position when said boss enters said first portion of said track from said second portion.

10. The medication injection pen according to claim 9, wherein
an audible indication is generated when said boss contacts an end of said first portion of said track when said indicator member is returned to said visible position.

11. The medication injection pen according to claim 2, wherein
a first boss extends outwardly from said indicator member;
an insert is fixed to said housing and has a second boss extending outwardly therefrom; and
a driver has a first track receiving said first boss and a second track receiving said second boss such that movement of said first boss in said first track moves said indicator member between said visible and said non-visible positions.

12. The medication injection pen according to claim 11, wherein
movement of said second boss in said second track of said driver facilitates rotation of said driver relative to said insert.

13. The medication injection pen according to claim 11, wherein
an arm extends axially from said driver toward said dose set knob.

14. The medication injection pen according to claim 3, wherein
a lug disposed on said dose set knob engages said arm when rotating said dose set knob to set a dose to move said indicator member from said visible to said non-visible position.

15. The medication injection pen according to claim 11, wherein
said first track has a first portion and a second portion, such that movement of said first boss through said first portion provides axial movement of said indicator member and movement of said first boss through said second portion prevents axial movement of said indicator member.

16. The medication injection pen according to claim 4, wherein
said lug has an angled surface; and
a protrusion disposed on said arm has an angled surface such that rotation of said dose set knob when setting said dose engages said angled surfaces to move said indicator member from said visible position to said non-visible position.

17. The medication injection pen according to claim 2, wherein
said spring is a torsion spring.

18. The medication injection pen according to claim 17, wherein
an insert is fixed to said housing and has a boss extending outwardly therefrom; and
a track disposed in said indicator member receives said boss such that movement of said boss in said track rotates said indicator member between said visible position and said non-visible position.

19. A medication injection pen, comprising:
a housing;
a dose set knob rotatably connected to said housing for setting a dose; and
a window disposed in said housing such that said dose set knob is visible in said window to indicate a zero position of said dose set knob and no portion of said dose set knob is visible in said window to indicate a non-zero position, said dose set knob being in said zero position when a set dose has been completely administered.

20. The medication injection pen according to claim 19, wherein
said dose set knob has a cut-out portion at a distal end thereof to facilitate visibility of said outer surface of said dose set knob through said window.

* * * * *